(12) United States Patent
Katoh et al.

(10) Patent No.: US 10,316,252 B2
(45) Date of Patent: *Jun. 11, 2019

(54) POLYMERIZABLE COMPOUND, POLYMER, POLYMERIZABLE COMPOSITION, AND FILM

(71) Applicant: FUJIFILM Corporation, Tokyo (JP)

(72) Inventors: Shunya Katoh, Ashigarakami-gun (JP); Daisuke Hayashi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/448,975

(22) Filed: Mar. 3, 2017

(65) Prior Publication Data

US 2017/0174991 A1 Jun. 22, 2017

Related U.S. Application Data

(63) Continuation of application No. PCT/JP2015/075153, filed on Sep. 4, 2015.

(30) Foreign Application Priority Data

Sep. 5, 2014 (JP) ................................ 2014-181137

(51) Int. Cl.

| | |
|---|---|
| *G02F 1/1333* | (2006.01) |
| *C09K 19/38* | (2006.01) |
| *C07C 69/92* | (2006.01) |
| *C07C 69/94* | (2006.01) |
| *C08F 20/30* | (2006.01) |
| *G02B 5/30* | (2006.01) |
| *C07C 69/54* | (2006.01) |
| *C08F 122/10* | (2006.01) |

(Continued)

(52) U.S. Cl.

CPC .......... *C09K 19/3852* (2013.01); *C07C 69/54* (2013.01); *C07C 69/92* (2013.01); *C07C 69/94* (2013.01); *C08F 20/30* (2013.01); *C08F 122/105* (2013.01); *C09K 19/38* (2013.01); *C09K 19/56* (2013.01); *C09K 19/586* (2013.01); *G02B 5/30* (2013.01); *G02B 5/3016* (2013.01); *C07C 2601/14* (2017.05)

(58) Field of Classification Search

CPC .... C09K 19/3852; C09K 19/38; C09K 19/56; C09K 19/586; C07C 69/92; C07C 69/94; C07C 69/54; C07C 2601/14; C08F 20/30; C08F 122/105; G02F 1/1333; G02B 5/30; G02B 5/3016

USPC .................................................... 252/299.63

See application file for complete search history.

(56) References Cited

U.S. PATENT DOCUMENTS

| | | |
|---|---|---|
| 6,338,902 B1 | 1/2002 | Hsu et al. |
| 6,395,351 B1 | 5/2002 | Benecke et al. |

(Continued)

FOREIGN PATENT DOCUMENTS

| | | |
|---|---|---|
| CN | 1257473 A | 6/2000 |
| CN | 101870651 A | 10/2010 |

(Continued)

OTHER PUBLICATIONS

Extended European Search Report (EESR) dated Dec. 1, 2017 from the European Patent Office in counterpart European Application No. 15837387.8.

(Continued)

*Primary Examiner* — Geraldina Visconti

(74) *Attorney, Agent, or Firm* — Sughrue Mion, PLLC

(57) ABSTRACT

The present invention provides a polymerizable compound represented by Formula (I), which can be used as a low birefringence liquid crystal;

(I)

$$Q^1-Sp^1-[Z^1-L^1]_{m1}-\underset{(R^1)_{n1}}{\text{Ar}}-O-C(=O)-\text{Cy}-$$

$$-\text{Cy}-C(=O)-O-\underset{(R^2)_{n2}}{\text{Ar}}-[L^2-Z^2]_{m2}-Sp^2-Q^2$$

in the formula, $R^1$ and $R^2$ represent $-C(=O)-X-Sp^3-Q^3$ or the like, n1 and n2 represent 0 to 4, X represents $-O-$ or the like, $Z^1$ represents an arylene group or the like, $Z^2$ represents an arylene group, or the like, m1 represents 1 or 2, m2 represents 0 to 2, $L^1$ and $L^2$ represent $-C(=O)O-$, $-OC(=O)-$, or the like, $Sp^1$, $Sp^2$, and $Sp^3$ represent an alkylene group, a group in which one or two or more $-CH_2-$'s in the alkylene group are substituted with $-O-$, or the like, $Q^1$ and $Q^2$ represent a polymerizable group, and $Q^3$ represents a hydrogen atom or a polymerizable group; a polymer obtained by polymerizing the polymerizable compound; a polymerizable composition containing the polymerizable compound; and a film formed of the polymerizable composition.

20 Claims, No Drawings

(51) Int. Cl.
    C09K 19/56    (2006.01)
    C09K 19/58    (2006.01)

(56) References Cited

U.S. PATENT DOCUMENTS

| | | | |
|---|---|---|---|
| 6,771,340 | B1 | 8/2004 | Yoshimi et al. |
| 6,791,645 | B2 | 9/2004 | Yano et al. |
| 7,927,671 | B2 | 4/2011 | Kato |
| 8,425,988 | B2 | 4/2013 | Hirai et al. |
| 8,771,810 | B2 | 7/2014 | Mizumura et al. |
| 9,505,980 | B2 | 11/2016 | Hirai et al. |
| 9,678,384 | B2 | 6/2017 | Ibaraki |
| 2002/0039159 | A1 | 4/2002 | Yano et al. |
| 2003/0178609 | A1 | 9/2003 | Hammond-Smith et al. |
| 2003/0224175 | A1 | 12/2003 | Morita et al. |
| 2005/0007541 | A1 | 1/2005 | Sasada et al. |
| 2009/0087590 | A1 | 4/2009 | Aiki et al. |
| 2011/0001088 | A1 | 1/2011 | Ootsuki et al. |
| 2013/0109825 | A1 | 5/2013 | Mizumura et al. |
| 2015/0175564 | A1 | 6/2015 | Sakamoto et al. |
| 2015/0344782 | A1 | 12/2015 | Matsuyama et al. |
| 2016/0318845 | A1 | 11/2016 | Katoh et al. |
| 2017/0009138 | A1 | 1/2017 | Nakazawa et al. |
| 2017/0174991 | A1 | 6/2017 | Katoh et al. |
| 2017/0190821 | A1 | 7/2017 | Katoh et al. |
| 2017/0242175 | A1 | 8/2017 | Ibaraki |
| 2017/0349828 | A1* | 12/2017 | Katoh ............... C09K 19/20 |

FOREIGN PATENT DOCUMENTS

| | | | |
|---|---|---|---|
| JP | 2002-042127 | A | 2/2001 |
| JP | 2001-527570 | A | 12/2001 |
| JP | 2002-107541 | A | 4/2002 |
| JP | 2003-315553 | A | 11/2003 |
| JP | 2004-262884 | A | 9/2004 |
| JP | 2005-99236 | A | 4/2005 |
| JP | 2006-096877 | A | 4/2006 |
| JP | 2009-098596 | A | 5/2009 |
| JP | 2009-244433 | A | 10/2009 |
| JP | 2010-024438 | A | 2/2010 |
| JP | 2010-270108 | A | 12/2010 |
| JP | 2011-237513 | A | 11/2011 |
| JP | 2013-216591 | A | 10/2013 |
| JP | 2016-053149 | A | 4/2016 |
| JP | 6080884 | B2 | 2/2017 |
| WO | 2011/162291 | A1 | 12/2011 |
| WO | 2014/010325 | A1 | 1/2014 |
| WO | 2014/142026 | A1 | 9/2014 |
| WO | 2015/115390 | A1 | 8/2015 |
| WO | 2015/147243 | A1 | 10/2015 |
| WO | 2016/047648 | A1 | 3/2016 |
| WO | 2017/007007 | A1 | 1/2017 |

OTHER PUBLICATIONS

Office Action dated Oct. 31, 2017, issued by the Japanese Patent Office in counterpart Japanese Application No. 2016-546701.
Partial Supplementary European Search Report dated Aug. 10, 2017, from the European Patent Office in counterpart European Application No. 15837387.8.
International Preliminary Report on Patentability with translation of written opinion dated Mar. 16, 2017 issued by the International Bureau in counterpart International Application No. PCT/JP2015/075153.
International Search Report of PCT/JP2015/075153 dated Nov. 24, 2015 [PCT/ISA/210].
Written Opinion of PCT/JP2015/075153 dated Nov. 24, 2015 [PCT/ISA/237].
Non-Final Office Action dated Aug. 10, 2017 from U.S. Appl. No. 15/273,784.
International Preliminary Report on Patentability dated Oct. 13, 2016 from the International Bureau in International Application No. PCT/JP2015/059559.
International Search Report for PCT/JP2015/059559 dated Jun. 30, 2015.
Written Opinion for PCT/JP2015/059559 dated Jun. 30, 2015.
Extended European Search Report issued by the EPO dated Aug. 2, 2017, in connection with European Patent Application No. 15844672.4.
International Preliminary Report on Patentability issued by WIPO dated Apr. 6, 2017 in connection with International Patent Application No. PCT/JP2015/076836.
International Search Report issued in PCT/JP2015/076836 dated Nov. 2, 2015.
Written Opinion issued in PCT/JP2015/076836 dated Nov. 2, 2015.
Non-Final Office Action issued in U.S. Appl. No. 14/886,740 dated Sep. 13, 2016.
Notice of Allowance issued in U.S. Appl. No. 14/886,740 dated Feb. 15, 2017.
Office Action dated Nov. 21, 2017 from the Japanese Patent Office in Japanese Application No. 2014-213749.
Office Action dated Nov. 21, 2017 from the Japanese Patent Office in Japanese Application No. 2014-214404.
International Preliminary on Patentability Report dated Sep. 12, 2017, issued by the International Searching Authority in Application No. PCT/JP2016/057696.
Written Opinion dated Jun. 14, 2016, issued by the International Searching Authority in Application No. PCT/JP2016/057696.
International Search Report dated Jun. 14, 2016, issued by the International Searching Authority in Application No. PCT/JP2016/057696.
Notice of Allowance dated Mar. 1, 2018 from U.S. Appl. No. 15/273,784.
Notice of Allowability dated May 10, 2018 from U.S. Appl. No. 15/273,784.
Office Action dated Sep. 5, 2018 from the State Intellectual Property Office of the P.R.C. In Chinese Application No. 201580049139.8, which corresponds to subject-matter related U.S. Appl. No. 15/465,829.
Non-Final Office Action dated Oct. 9, 2018 from the U.S. Patent and Trademark Office in subject-matter related U.S. Appl. No. 15/590,401.
Office Action dated Sep. 28, 2018 from the United States Patent and Trademark Office in co-pending U.S. Appl. No. 15/465,829.
Office Action dated Jun. 26, 2018, from the State Intellectual Property Office of People's Republic of China in counterpart Chinese Application No. 201580045362.5.
Notification of Reasons for Refusal dated Sep. 4, 2018 from the Japanese Patent Office in Japanese application No. 2014-214404.
Decision of Refusal dated Sep. 4, 2018 from the Japanese Patent Office in Japanese application No. 2014-213749.
Office Action dated Mar. 6, 2018, from Japanese Patent Office in counterpart Japanese Application No. 2016-546701.
Office Action dated Dec. 4, 2018 from the Japanese Patent Office in JP Application No. 2017-505414 (corresponds to U.S. Appl. No. 15/685,530).
Office Action dated Mar. 1, 2019, from the U.S. Patent and Trademark Office in co-pending U.S. Appl. No. 15/685,530.
Office Action dated Feb. 15, 2019, from State Intellectual Property Office of the P.R.C. In counterpart Chinese Application No. 201580045362.5.
Office Action dated Jan. 29, 2019 from the United States Patent and Trademark Office in co-pending U.S. Appl. No. 15/590,401.
Office Action dated Feb. 3, 2019 from the State Intellectual Property Office of the P.R.C. In Chinese Application No. 201580049139.8.

* cited by examiner

POLYMERIZABLE COMPOUND, POLYMER, POLYMERIZABLE COMPOSITION, AND FILM

CROSS-REFERENCE TO RELATED APPLICATIONS

This application is a continuation of PCT International Application No. PCT/JP2015/075153 filed on Sep. 4, 2015, which claims priority under 35 U.S.C. § 119 (a) to Japanese Patent Application No. 2014-181137 filed on Sep. 5, 2014, the entire content of which is incorporated herein by reference.

BACKGROUND OF THE INVENTION

1. Field of the Invention

The present invention relates to a novel polymerizable compound. In addition, the present invention relates to a polymer manufactured from the novel polymerizable compound, a polymerizable composition containing the novel polymerizable compound, and a film formed of the polymerizable composition containing the novel polymerizable compound.

2. Description of the Related Art

It is possible to prepare various optical films such as a phase difference film or a reflection film by using a polymerizable compound having liquid crystallinity. The birefringence of the polymerizable compound is one of properties closely associated with the optical properties of an optical film to be obtained. For example, it is possible to obtain a phase difference film having a thin film thickness and desired phase difference by using a liquid crystal having high birefringence (WO2011/162291A).

On the other hand, it is possible to obtain a reflection film having high selectivity in a reflection wavelength range with a film which is formed by using a polymerizable compound having low birefringence and by immobilizing a cholesteric liquid crystalline phase. In JP2004-262884A, it is disclosed that a low birefringence phase difference film, or a reflection film having high selectivity in a reflection wavelength range is obtained by using a non-liquid crystalline (meth)acrylate compound having a specific structure along with a polymerizable liquid crystal compound.

SUMMARY OF THE INVENTION

An object of the present invention is to provide a novel polymerizable compound which can be used as a low birefringence liquid crystal. In addition, another object of the present invention is to provide a film such as a low birefringence phase difference film which is prepared by using the novel polymerizable compound.

The present inventors have studied compounds having various structures in order to attain the objects described above, and thus, have found that a novel compound having a structure similar to that of a known polymerizable compound in JP2003-315553A has low birefringence, and has properties advantageous to the formation of a film, have further conducted studies on the basis of the findings, and thus, have completed the present invention.

That is, the present invention provides <1> to <17> described below.

<1> A polymerizable compound represented by Formula (I).

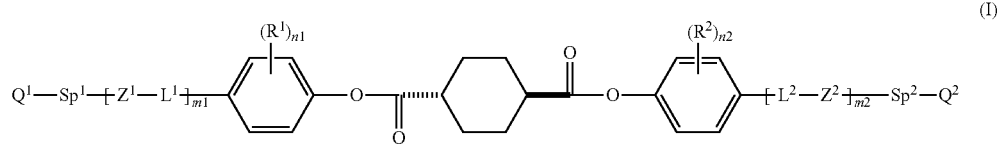

In the formula, $R^1$ and $R^2$ are each independently a group selected from the group consisting of an alkyl group, an alkoxy group, and $—C(=O)—X-Sp^3-Q^3$, n1 and n2 each independently represent an integer of 0 to 4, X represents a single bond, —O—, —S—, or —N(Sp$^4$-Q$^4$)-, or represents a nitrogen atom which forms a cyclic structure along with Q$^3$ and Sp$^3$, $Z^1$ represents an arylene group which may have a substituent or a heteroarylene group which may have a substituent, $Z^2$ represents a trans-1,4-cyclohexylene group which may have a substituent, an arylene group which may have a substituent, or a heteroarylene group which may have a substituent, all of the substituents are each independently 1 to 4 substituents selected from the group consisting of an alkyl group, an alkoxy group, and $—C(=O)—X-Sp^3-Q^3$, m1 represents an integer of 1 or 2, and m2 represents an integer of 0 to 2, when m1 and m2 represent 2, two $Z^1$'s and $Z^2$'s may be identical to each other or different from each other, $L^1$ and $L^2$ each independently represent a single bond or a linking group selected from the group consisting of —O—, —CH$_2$O—, —OCH$_2$—, —(CH$_2$)$_2$OC(=O)—, —C(=O)O(CH$_2$)$_2$—, —NH—, N(CH$_3$)—, —S—, —C(=O)O—, —OC(=O)—, —OC(=O)O—, —C(=O)N(T$^3$)-, —N(T$^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, T$^3$ represents -Sp$^5$-Q$^5$, Sp$^1$, Sp$^2$, Sp$^3$, Sp$^4$, and Sp$^5$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, $Q^1$ and $Q^2$ each independently represent any one polymerizable group selected from the group consisting of groups represented by Formula (Q-1) to Formula (Q-5) below, and $Q^3$, $Q^4$, and $Q^5$ each independently represent any one polymerizable group selected from the group consisting of a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or groups represented by Formula (Q-1) to Formula (Q-5) below, and may represent a single bond in a case in which Q$^3$ forms a cyclic structure along with X and Sp$^3$, and when Sp$^4$ is a single bond, Q$^4$ is not a hydrogen atom.

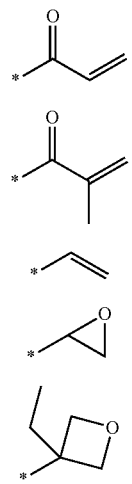

<2> The polymerizable compound according to <1>, in which R$^1$ and R$^2$ are each —C(=O)—X-Sp$^3$-Q$^3$.

<3> The polymerizable compound according to <2>, in which X is —O—.

<4> The polymerizable compound according to <2> or <3>, in which Sp$^3$ is any one group selected from the group consisting of a linear alkylene group or a branched alkylene group having 1 to 5 carbon atoms, —(CH$_2$)$_2$—O—(CH$_2$)$_2$—, —CH$_2$—O—(CH$_2$)$_2$—, and —(CH$_2$)$_2$—O—CH$_2$—.

<5> The polymerizable compound according to any one of <1> to <4>, in which m1 is 1, and Z$^1$ is an arylene group which may have a substituent.

<6> The polymerizable compound according to any one of <1> to <5>, in which Q$^1$ and Q$^2$ are each independently a group represented by Formula (Q-1) or a group represented by Formula (Q-2).

<7> The polymerizable compound according to any one of <1> to <6>, in which m2 is 0 or 1, and Z$^2$ is an arylene group which may have a substituent.

<8> The polymerizable compound according to any one of <1> to <7>, in which both of L$^1$ and L$^2$ are —C(=O)O— or —OC(=O)—.

<9> The polymerizable compound according to <1>, in which R$^1$ and R$^2$ are each —C(=O)—O-Sp$^3$-Q$^3$, Sp$^3$ is any one group selected from the group consisting of a linear alkylene group or a branched alkylene group having 1 to 5 carbon atoms, —(CH$_2$)$_2$—O—(CH$_2$)$_2$—, —CH$_2$—O—(CH$_2$)$_2$—, and —(CH$_2$)$_2$—O—CH$_2$—, m1 is 1, and Z$^1$ is a phenylene group which may have a substituent, Q$^1$ and Q$^2$ are each independently a group represented by Formula (Q-1) or a group represented by Formula (Q-2), and both of L$^1$ and L$^2$ are —C(=O)O— or —OC(=O)—.

<10> The polymerizable compound according to <9>, in which m2 is 0 or 1, and Z$^2$ is a phenylene group which may have a substituent.

<11> A polymer obtained by a polymerization reaction of the polymerizable compound according to any one of <1> to <10>.

<12> A polymerizable composition, comprising:
the polymerizable compound according to any one of <1> to <10>.

<13> The polymerizable composition according to <10>, further comprising: any other liquid crystal compound along with the polymerizable compound represented by Formula (I).

<14> The polymerizable composition according to <12> or <13>, further comprising: a cross-linking agent.

<15> The polymerizable composition according to any one of <12> to <14>, further comprising: a polymerization initiator.

<16> The polymerizable composition according to any one of <12> to <15>, further comprising: a chiral compound.

<17> A film, comprising: a cured film of the polymerizable composition according to any one of <12> to <16>.

According to the present invention, a novel polymerizable compound which can be used as a low birefringence liquid crystal is provided. It is possible to manufacture a novel polymer by using the polymerizable compound, and it is possible to provide a novel film such as a low birefringence phase difference film by using a polymerizable composition containing the polymerizable compound.

DESCRIPTION OF THE PREFERRED EMBODIMENTS

Hereinafter, the present invention will be described in detail. Furthermore, herein, a numerical range represented by using "to" indicates a range including the numerical values before and after "to" as the lower limit value and the upper limit value.

Herein, "(meth)acrylate" indicates "any one or both of acrylate and methacrylate". The same applies to "(meth)acryl group" or the like, and "(meth)acryloyl group" indicates "any one or both of an acryloyl group and a methacryloyl group".

Herein, a phase difference indicates in-plane retardation, and indicates in-plane retardation at a wavelength of 550 nm, unless otherwise a wavelength is stated. Herein, the in-plane retardation is measured by using a polarization phase difference analysis device AxoScan manufactured by Axometrics, Inc. The in-plane retardation at a wavelength of λ nm can be measured by allowing light at a wavelength of λ nm to be incident in a film normal direction using KOBRA 21ADH or WR (manufactured by Oji Scientific Instruments).

<Polymerizable Compound Represented by Formula (I)>
Hereinafter, each group in Formula (I) will be described.
Furthermore, a steric cyclohexyl group in Formula (I) indicates relative arrangement, that is, indicates a trans form (a trans-1,4-cyclohexylene group).

R$^1$ and R$^2$ are each independently a group selected from the group consisting of an alkyl group, an alkoxy group, and —C(=O)—X-Sp$^3$-Q$^3$.

Herein, the alkyl group may be any one of a linear alkyl group and a branched alkyl group. The number of carbon atoms of the alkyl group is preferably 1 to 30, is more preferably 1 to 10, and is particularly preferably 1 to 6. Examples of the alkyl group can include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a 1,1-dimethyl propyl group, an n-hexyl group, an isohexyl group, a linear heptyl group or a branched heptyl group, an octyl group, a nonyl group, a decyl group, a undecyl group, or a dodecyl group. The same description with respect to the alkyl group described above applies to an alkoxy group including the alkyl group. In addition, the alkylene group is a group obtained by removing an arbitrary hydrogen atom from the alkyl group, and examples of the alkylene group can include groups obtained by removing an arbitrary hydrogen atom from each of the examples of the alkyl group described above.

Herein, the number of carbon atoms of the cycloalkyl group is preferably 3 to 20, is more preferably greater than or equal to 5, and is preferably less than or equal to 10, is more preferably less than or equal to 8, and is even more preferably less than or equal to 6. Examples of the cycloalkyl group can include a cyclopropyl group, a cyclobutyl group, a cyclopentyl group, a cyclohexyl group, a cycloheptyl group, and a cyclooctyl group.

n1 and n2 each independently represent an integer of 0 to 4, are preferably an integer of 0 to 3, and are more preferably 0 or 1. When $R^1$ is —C(=O)—X-$Sp^3$-$Q^3$, it is preferable that n1 is 1, and when $R^2$ is —C(=O)—X-$Sp^3$-$Q^3$, it is preferable that n2 is 1. When both of $R^1$ and $R^2$ are —C(=O)—X-$Sp^3$-$Q^3$, it is preferable that n1+n2 is 1 or 2. —C(=O)—X-$Sp^3$-$Q^3$, a methyl group, or a methoxy group is preferable, and —C(=O)—X-$Sp^3$-$Q^3$ is more preferable, as each of $R^1$ and $R^2$. When $R^1$ is an alkyl group having 1 to 3 carbon atoms, it is preferable that n1 is 3, and when $R^2$ is an alkyl group having 1 to 3 carbon atoms, it is preferable that n2 is 3.

X represents a single bond, —O—, —S—, or —N($Sp^4$-$Q^4$)-, or represents a nitrogen atom which forms a cyclic structure along with $Q^3$ and $Sp^3$. —O— or —N($Sp^4$-$Q^4$)- is preferable, and —O— is more preferable, as X.

$Z^1$ represents an arylene group which may have a substituent or a heteroarylene group which may have a substituent, and $Z^2$ represents a 1,4-cyclohexylene group which may have a substituent, an arylene group which may have a substituent, or a heteroarylene group which may have a substituent.

The arylene group is a divalent group configured by removing two hydrogen atoms (hydrogen radicals) from an aromatic compound. It is preferable that the aromatic compound is a 5-membered ring to a 18-membered ring. In addition, the heteroarylene group is a divalent group configured by removing two hydrogen atoms (hydrogen radicals) from an aromatic heterocyclic compound. It is preferable that the aromatic heterocyclic compound is a 5-membered ring to a 18-membered ring.

Hereinafter, examples of the aromatic compound and the aromatic heterocyclic compound will be described, but the present invention is not limited thereto.

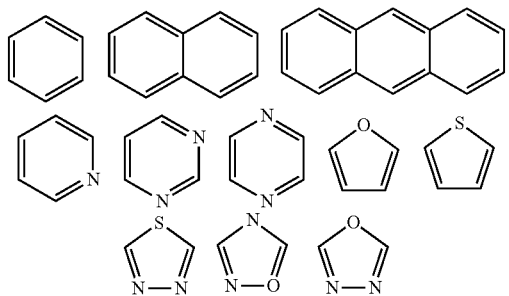

In the arylene group, the heteroarylene group, and the trans-1,4-cyclohexylene group "which may have a substituent", all of the substituents are a substituent selected from the group consisting of alkyl group, an alkoxy group, and —C(=O)—X-$Sp^3$-$Q^3$. In addition, the number of substituents may be 1 to 4. When the number of substituents is greater than or equal to 2, two or more substituents may be identical to each other or different from each other.

$Z^1$ is preferably an arylene group which may have a substituent, and is more preferably a non-substitutional arylene group. $Z^2$ is preferably a trans-1,4-cyclohexylene group which may have a substituent or an arylene group which may have a substituent, is more preferably a non-substitutional trans-1,4-cyclohexylene group or a non-substitutional arylene group, and is even more preferably a non-substitutional arylene group.

A phenylene group is particularly preferable as the arylene group, and in particular, a 1,4-phenylene group is preferable.

m1 represents an integer of 1 or 2, m2 represents an integer of 0 to 2, and when m1 or m2 represents 2, two $Z^1$'s and $Z^2$'s may be identical to each other or different from each other. A structure is preferable in which m1 is 1, and m2 is 0 or 1. That is, it is preferable that the polymerizable compound represented by Formula (I) has 4 or 5 cyclic structures. It is more preferable that the number of cyclic structures is 5.

$L^1$ and $L^2$ each independently represent a single bond or a linking group selected from the group consisting of —O—, —CH$_2$O—, —OCH$_2$—, —(CH$_2$)$_2$OC(=O)—, —C(=O)O(CH$_2$)$_2$—, —NH—, N(CH$_3$)—, —S—, —C(=O)O—, —OC(=O)—, —OC(=O)O—, —C(=O)N($T^3$)-, —N($T^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—. Furthermore, herein, when a divalent linking group is described as described above, a direct bond on a left side (in a case of "—CH$_2$O—", "C") is on a $Q^1$ side in Formula (I), and a direct bond on a right side (in a case of "—CH$_2$O—", "O") is on a $Q^2$ side in Formula (I). It is preferable that $L^1$ and $L^2$ are each independently —C(=O)O— or —OC(=O)—, and in particular, it is preferable that $L^1$ is —C(=O)O— and $L^2$ is —OC(=O)—.

$T^3$ represents -$Sp^5$-$Q^5$, and is preferably a hydrogen atom ($Sp^5$ is a single bond, and $Q^5$ is a hydrogen atom).

$Sp^1$, $Sp^2$, $Sp^3$, $Sp^4$, and $Sp^5$ each independently represent a single bond or a linking group selected from the group consisting of a linear alkylene group or a branched alkylene group having 1 to 20 carbon atoms, and a group in which one or two or more —CH$_2$—'s in the linear or the branched alkylene group having 1 to 20 carbon atoms are substituted with —O—, —S—, —NH—, —N(CH$_3$)—, —C(=O)—, —OC(=O)—, or —C(=O)O—.

It is preferable that $Sp^1$ and $Sp^2$ are each independently a linking group configured by combining one or two or more groups selected from the group consisting of a linear alkylene group having 1 to 10 carbon atoms in which a linking group selected from the group consisting of —O—, —OC(=O)—, and —C(=O)O— is bonded to both terminals, —OC(=O)—, —C(=O)O—, —O—, and a linear alkylene group having 1 to 10 carbon atoms, and it is more preferable that $Sp^1$ and $Sp^2$ are each independently a linear alkylene group having 1 to 10 carbon atoms in which —O— is bonded to each of both terminals.

A linear alkylene group or a branched alkylene group having 1 to 10 carbon atoms or a group in which two linear alkylene groups having 1 to 10 carbon atoms are bonded by —O— is preferable, and a linear alkylene group or a branched alkylene group having 1 to 5 carbon atoms, —(CH$_2$)$_2$—O—(CH$_2$)$_2$—, —CH$_2$—O—(CH$_2$)$_2$—, or —(CH$_2$)$_2$—O—CH$_2$— is more preferable, as Sp$^3$.

It is preferable that Sp$^4$ and Sp$^5$ are each independently a linear alkylene group or a branched alkylene group having 1 to 10 carbon atoms, it is more preferable that Sp$^4$ and Sp$^5$ each independently a linear alkylene group having 1 to 5 carbon atoms, and it is even more preferable that Sp$^4$ and Sp$^5$ each independently a linear alkylene group having 1 to 3 carbon atoms.

Q$^1$ and Q$^2$ each independently represent any one polymerizable group selected from the group consisting of groups represented by Formula (Q-1) to Formula (Q-5) below. Q$^3$, Q$^4$, and Q$^5$ represent any one polymerizable group selected from the group consisting of a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or groups represented by Formula (Q-1) to Formula (Q-5) below.

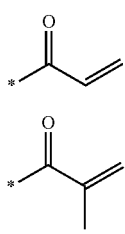

(Q-1)

(Q-2)

(Q-3)

(Q-4)

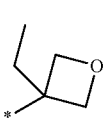

(Q-5)

Specifically, examples of the group in which one or two or more —CH$_2$—'s in the cycloalkyl group are substituted with —O—, —S—, —NH—, —N(CH$_3$)—, —C(=O)—, —OC(=O)—, or —C(=O)O— include a tetrahydrofuranyl group, a pyrrolidinyl group, an imidazolidinyl group, a pyrazolidinyl group, a piperidyl group, a piperazinyl group, a morpholinyl group, and the like. A substitution position is not particularly limited. Among them, the tetrahydrofuranyl group is preferable, and a 2-tetrahydrofuranyl group is particularly preferable.

In a case where X is a nitrogen atom which forms a cyclic structure along with Q$^3$ and Sp$^3$, Q$^3$ may represent a single bond. When Sp$^4$ is a single bond, Q$^4$ is not a hydrogen atom, that is, X does not represent —NH—.

An acryloyl group (formula (Q-1)) or a methacryloyl group (formula (Q-2)) is preferable as the polymerizable group.

In addition, it is preferable that Q$^3$, Q$^4$, and Q$^5$ are each a hydrogen atom.

Hereinafter, examples of the polymerizable compound represented by Formula (I) will be described, but the polymerizable compound is not limited thereto.

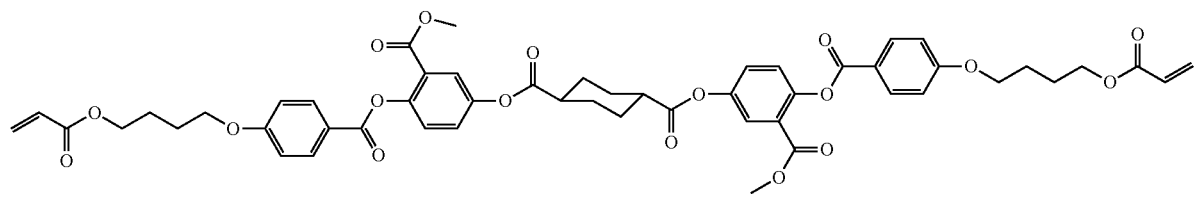

1

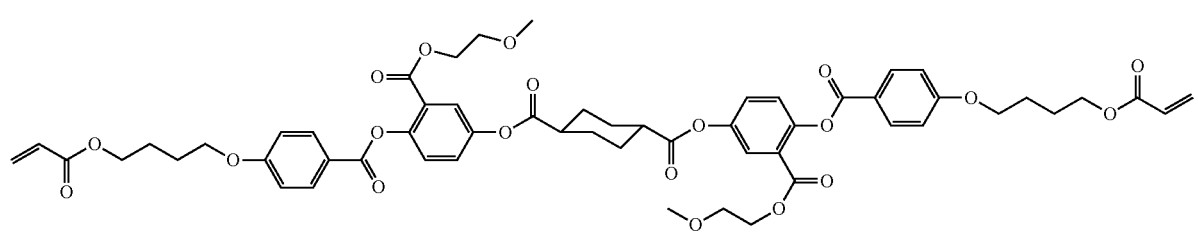

2

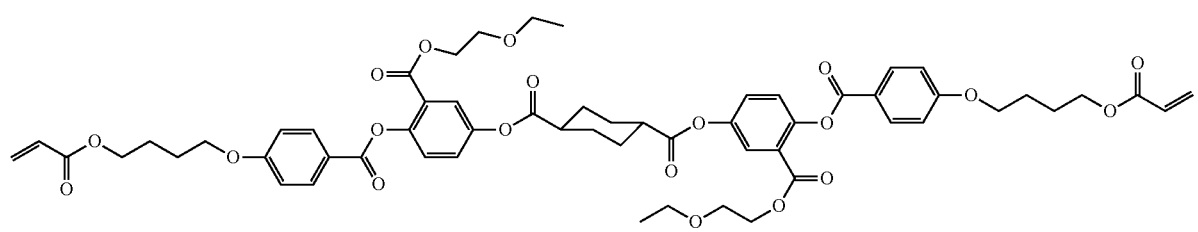

3

-continued
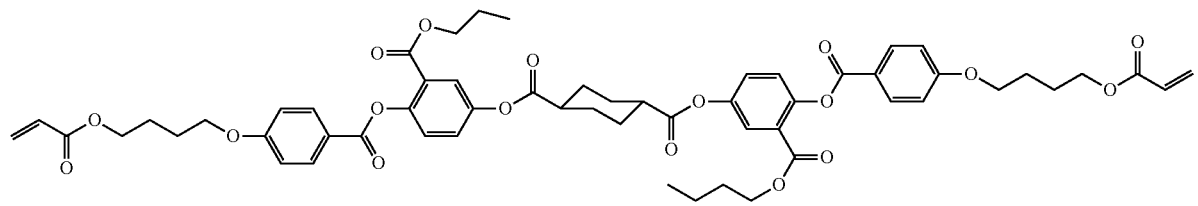
4
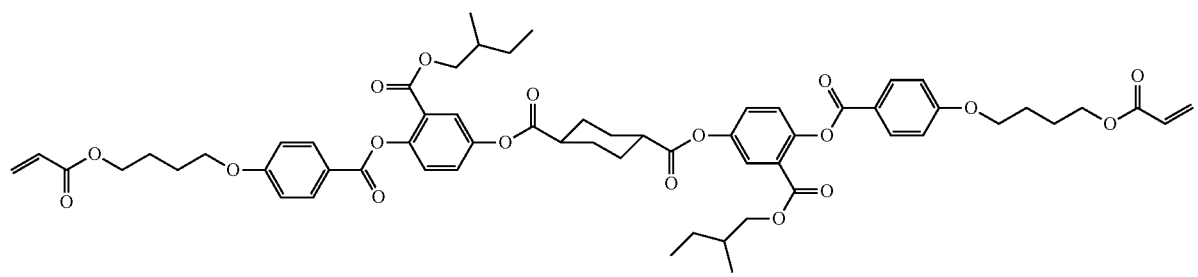
5
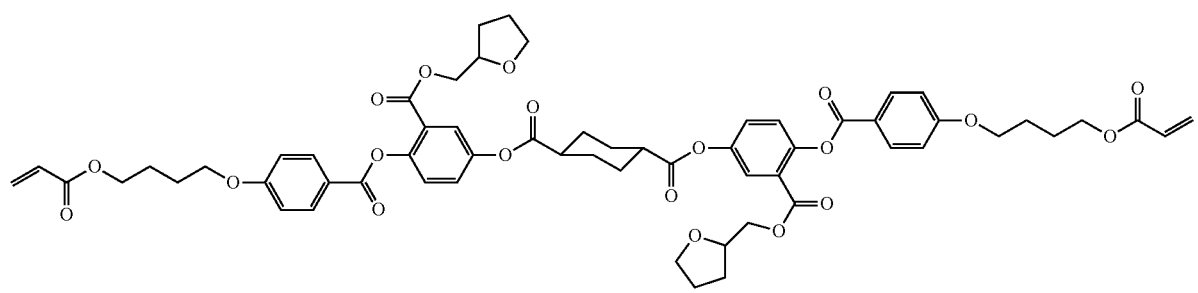
6
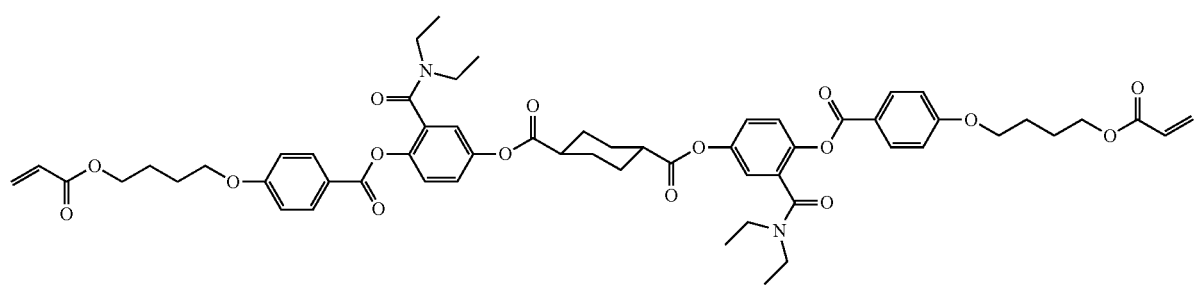
7
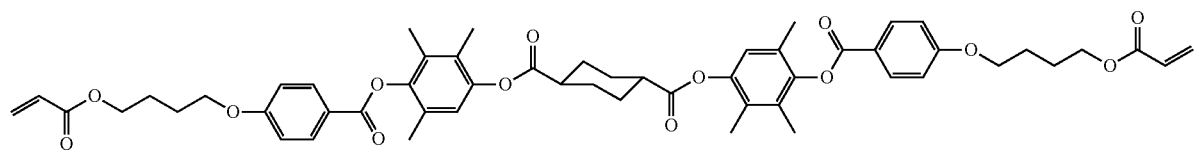
8
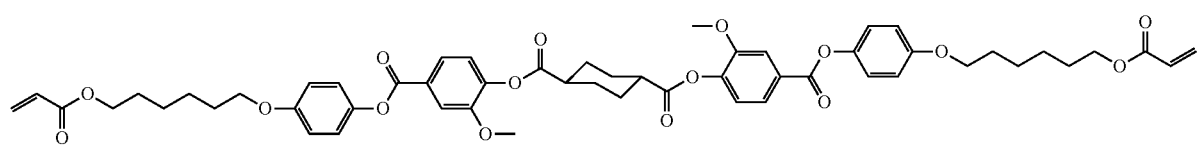
9

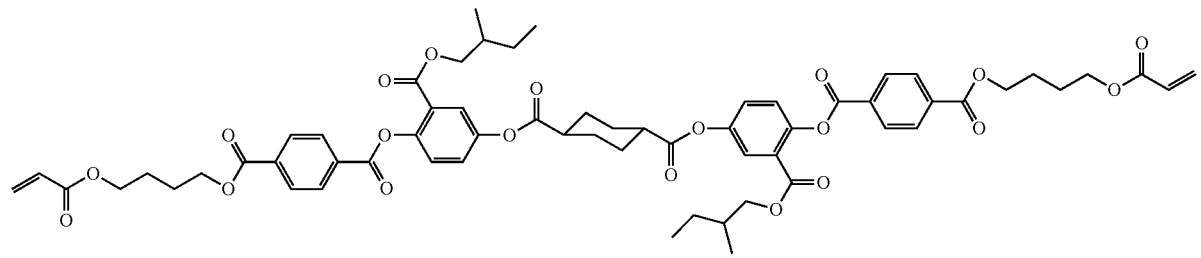
10
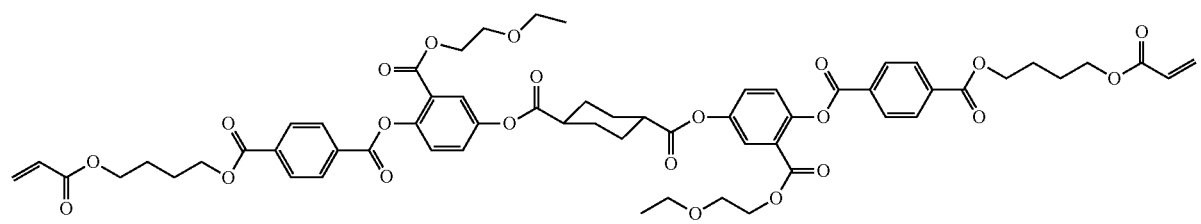
11
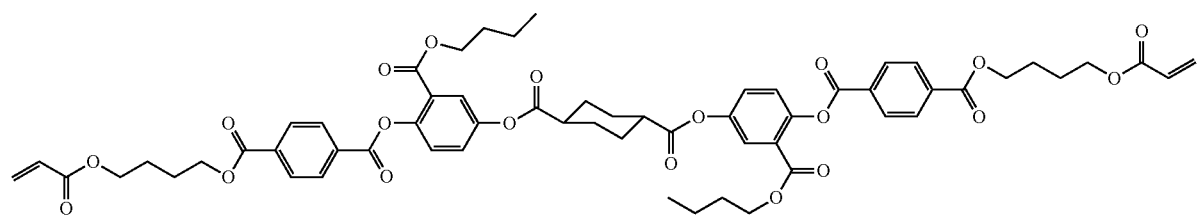
12
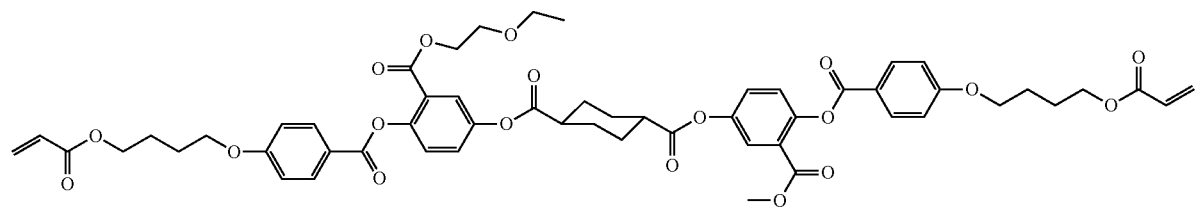
13
14
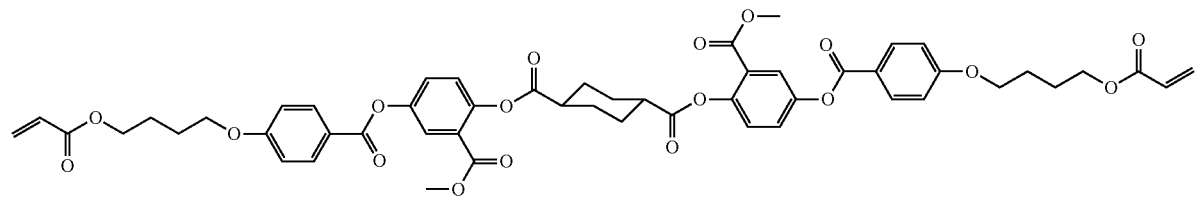
15

-continued
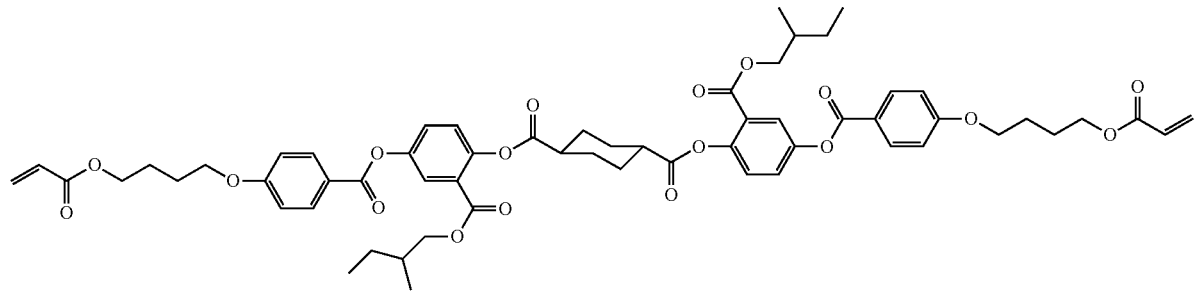
16
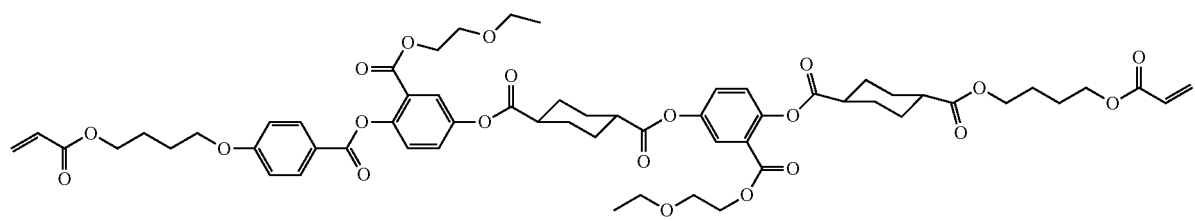
17
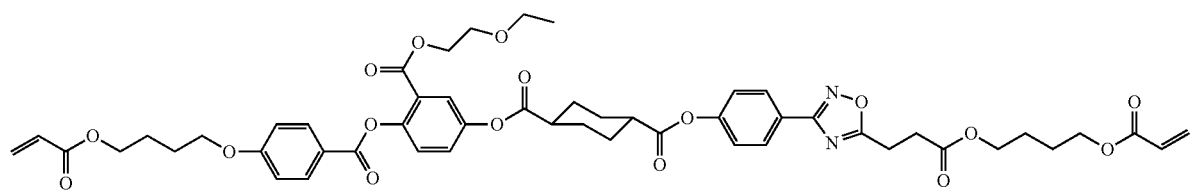
18
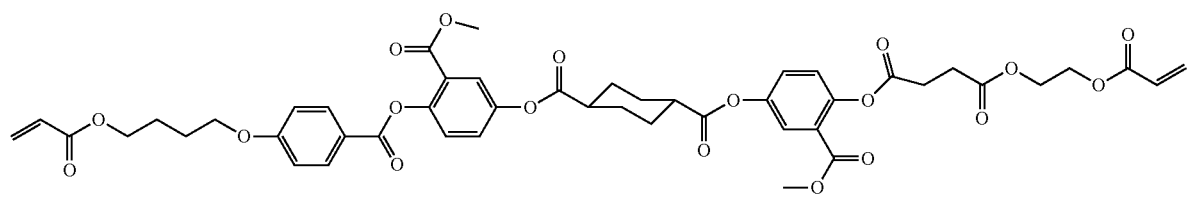
19
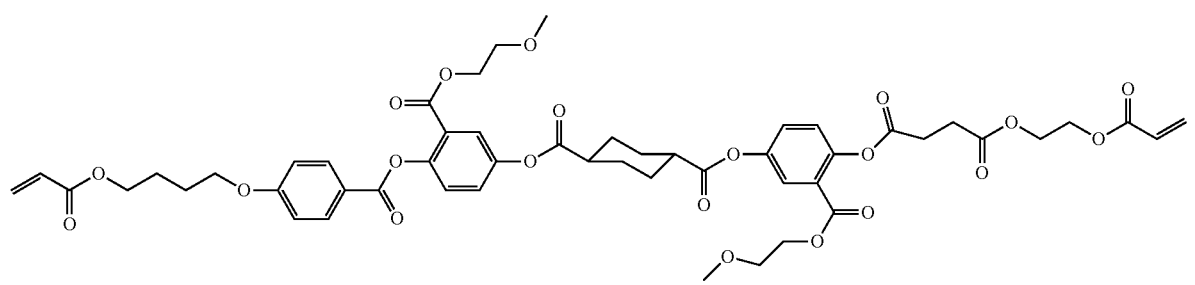
20
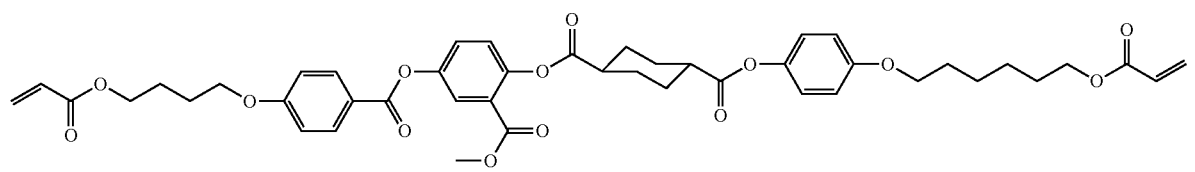
21

-continued

22

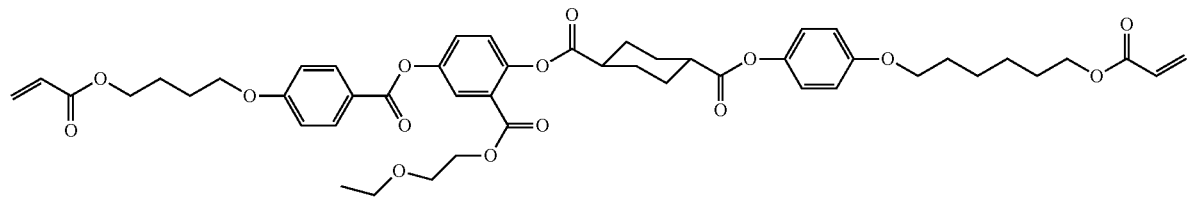

23

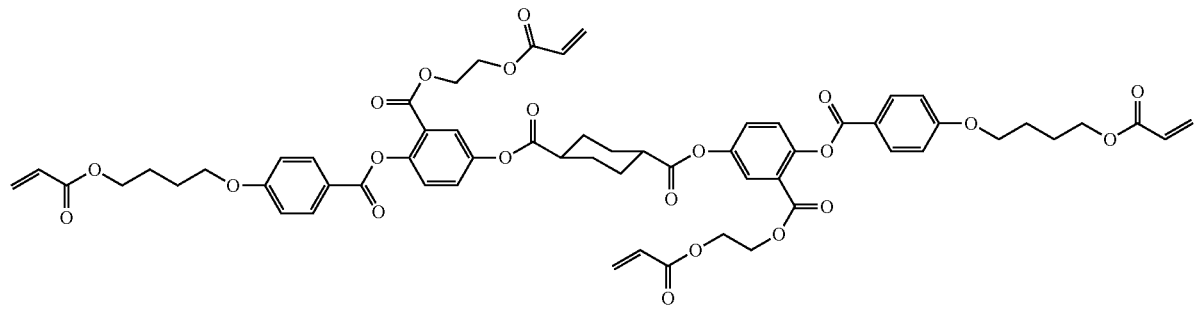

24

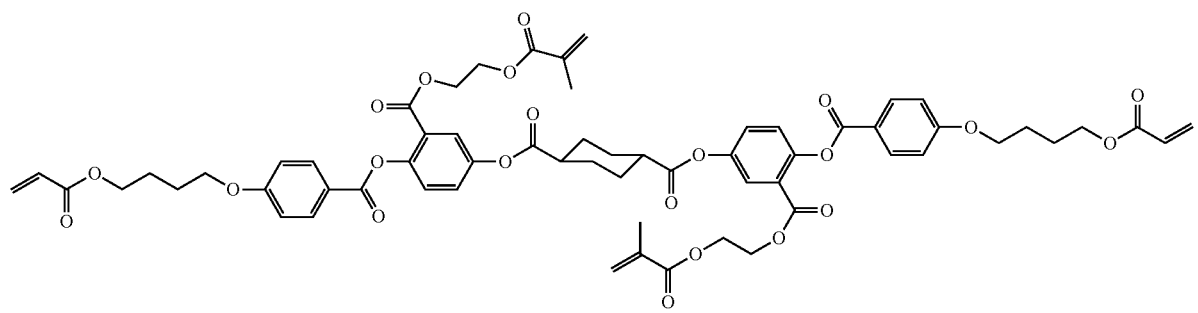

25

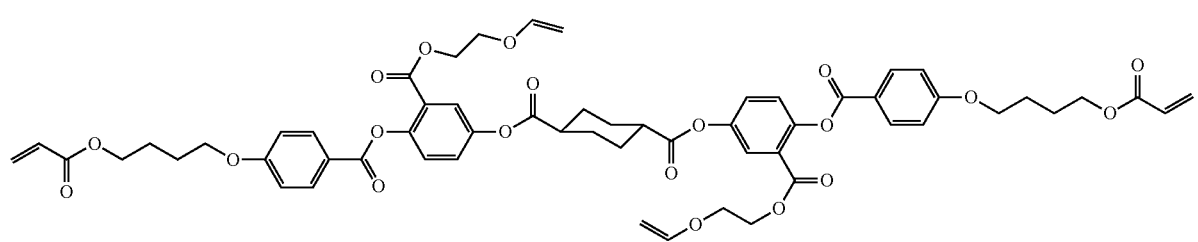

26

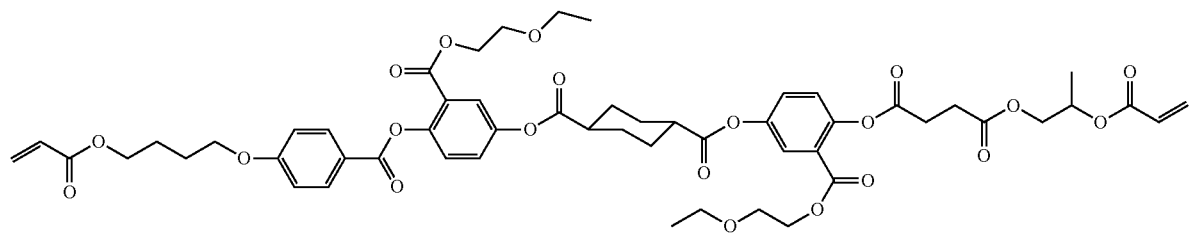

Among the exemplified compounds described above, compounds 1, 2, 3, 4, 5, 17, 23, 24, and 26 are preferable, the compounds 1, 2, 3, 4, 5, 17, 23, and 24 are more preferable, and the compound 3, 23, and 24 are even more preferable.

The polymerizable compound represented by Formula (I) can be manufactured by a known method. For example, as described below, the polymerizable compound represented by Formula (I) can be manufactured by a method through an intermediate A using a trans-1,4-cyclohexane dicarboxylic acid and phenol B as a starting raw material.

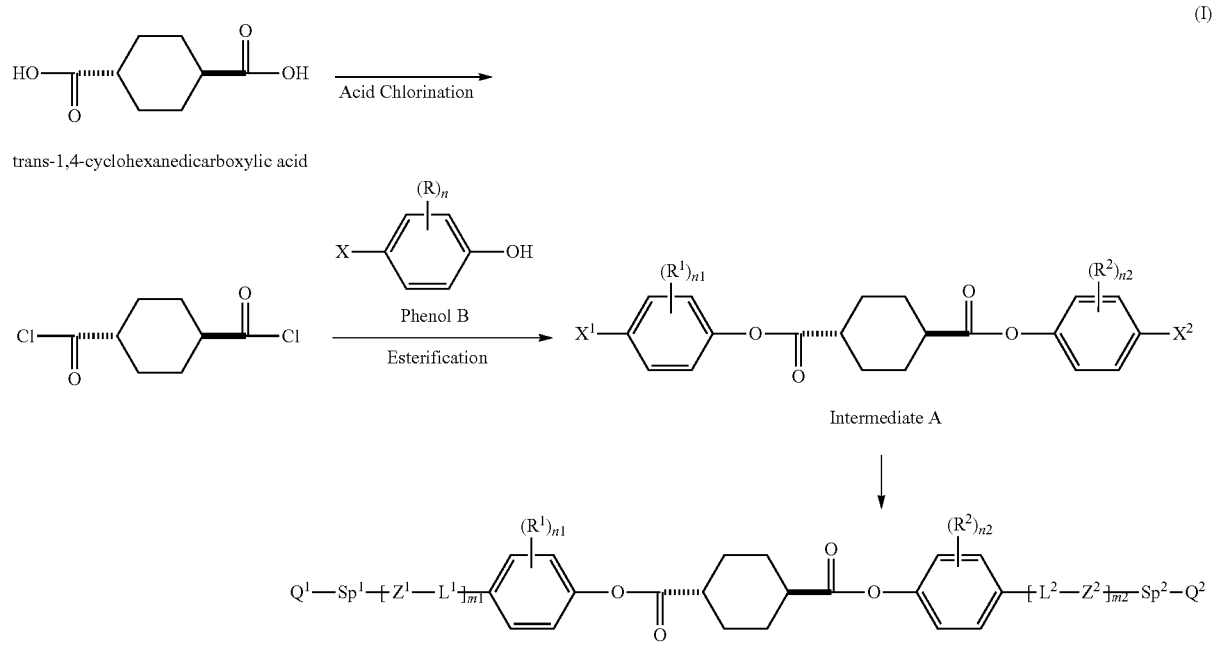

A case where $L^1$ in Formula (I) is —COO— and $L^2$ in Formula (I) is —OCO— will be described in detail as an example.

First, in the manufacturing of the intermediate A, phenol B which is a raw material of the intermediate A is 1,4-diphenol, and it is preferable that only one phenol of the 1,4-diphenol is preferentially subjected to a reaction from the viewpoint of preventing sub-generation of a polymer. Specifically, it is preferable that the phenol B is excessively used, one hydroxyl group is protected as described below, or phenol B having a structure in which a substituent R represents —C(=O)—X-Sp$^3$-Q$^3$ is used.

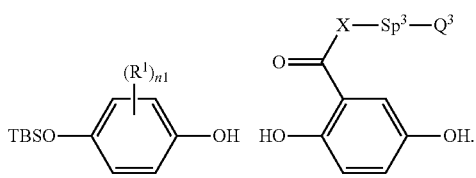

Phenol B of which One Side is Protected Phenol B in which R has Specific Structure For example, a t-butyl dimethyl silyl group or the like can be used as a protective group of the hydroxyl group. In a case where R represents —C(=O)—X-Sp$^3$-Q$^3$, a difference occurs in the reactivities of the hydroxyl groups in an ortho position and a meta position of R, and thus, it is possible to perform a reaction with respect to only one hydroxyl group even in a case where the hydroxyl group is not protected.

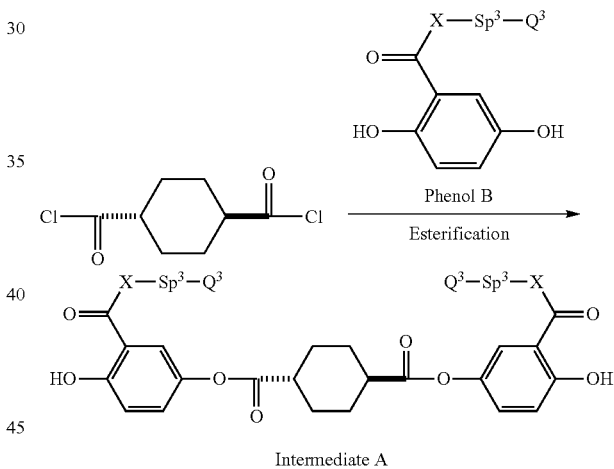

A structure in which the substituent R represents —C(=O)—X-Sp$^3$-Q$^3$ is preferable as the structure of the phenol B since a protecting step can be omitted.

Next, in the manufacturing of the polymerizable compound represented by Formula (I), examples of a method of performing esterification between a carboxylic acid C and the intermediate A include a method in which the carboxylic acid C is activated, and is allowed to act in the presence of a base along with the intermediate A, and a method in which the carboxylic acid C and the intermediate A are directly esterified by using a condensation agent such as carbodiimide.

Examples of a method of activating the carboxylic acid C include a method in which a mixed acid anhydride is prepared by performing acid chlorination or by allowing mesyl chloride to act by using thionyl chloride, oxalyl chloride, or the like.

The method of activating the carboxylic acid C is more preferable from the viewpoint of a by-product.

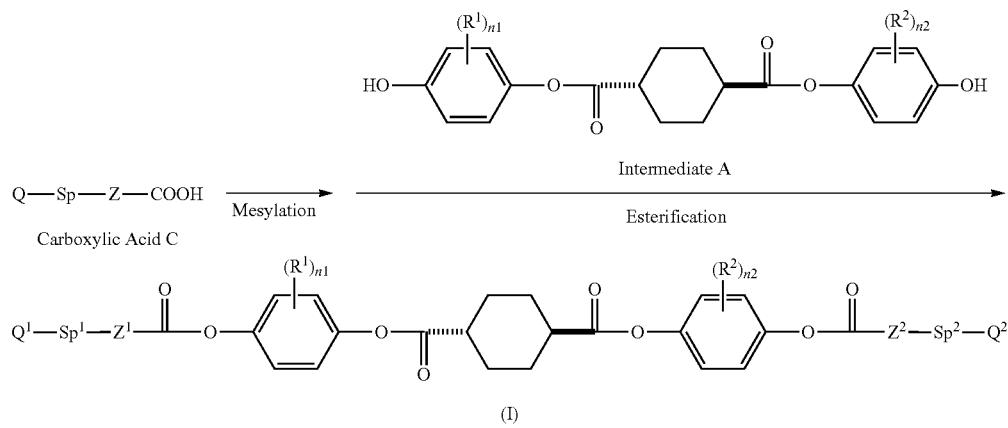

The polymerizable compound represented by Formula (I) has liquid crystallinity and low birefringence, and thus, the birefringence of a phase difference film can be adjusted to be in a desired range by preparing the phase difference film by using the polymerizable compound represented by Formula (I). In particular, a cholesteric liquid crystalline phase is formed by using the polymerizable compound represented by Formula (I), and a film is formed by immobilizing the cholesteric liquid crystalline phase, and thus, it is possible to obtain a reflection film having a narrow wavelength range of selective reflection, that is, a reflection film having high selectivity in a reflection wavelength range.

In addition, the polymerizable compound represented by Formula (I) satisfies a plurality of properties such as being colorless and transparent, having a wide liquid crystalline phase range, being easily dissolved in a solvent, and being easily polymerized, since absorption in a visible light range is extremely low regardless of the type of substituent of an aromatic ring or a linking group. According to this, a cured film which is prepared by using a polymerizable composition containing the polymerizable compound represented by Formula (I) can satisfy a plurality of properties such as having a sufficient hardness, being colorless and transparent, having excellent weather fastness and excellent heat resistance. Accordingly, the cured film formed by using the polymerizable composition described above, for example, can be used in various applications such as a phase difference plate, a polarization element, a selective reflection film, a color filter, an antireflection film, a view angle compensation film, a holography, and an alignment film which are constituents of an optical element.

<Polymerizable Composition>

In the polymerizable composition, only one type of the polymerizable compound represented by Formula (I) may be contained, or two or more types thereof may be contained.

The content of the polymerizable compound represented by Formula (I) (in a case where two or more types of the polymerizable compounds represented by Formula (I) are contained, the total amount of the two or more types of the polymerizable compounds) may be greater than or equal to 10 mass %, is preferably 30 to 99.9 mass %, is more preferably 50 to 99.5 mass %, and is even more preferably 70 to 99 mass %, with respect to the mass of solid contents of the polymerizable composition. Here, the content of the polymerizable compound represented by Formula (I) is not limited to the range described above.

The polymerizable composition may contain other components such as other liquid crystal compounds, a chiral compound, a polymerization initiator, and an alignment control agent, in addition to the polymerizable compound represented by Formula (I). Hereinafter, each component will be described.

[Other Liquid Crystal Compounds]

The polymerizable composition may contain one or more other liquid crystal compounds along with the polymerizable compound represented by Formula (I). The polymerizable compound represented by Formula (I) has high compatibility with respect to the other liquid crystal compounds, and thus, even in a case of being mixed with the other liquid crystal compounds, it is possible to form a film having high transparency without the occurrence of opacification or the like. The other liquid crystal compounds can be used together, and thus, it is possible to provide compositions having various compositions suitable for various applications. Examples of the other liquid crystal compounds which can be used together include a rod-like nematic liquid crystal compound. Examples of the rod-like nematic liquid crystal compound include azomethines, azoxies, cyanobiphenyls, cyanophenyl esters, benzoic acid esters, phenyl cyclohexane carboxylic acid esters, cyanophenyl cyclohexanes, cyano-substituted phenyl pyrimidines, alkoxy-substituted phenyl pyrimidines, phenyl dioxanes, tolans, and alkenyl cyclohexyl benzonitriles. It is possible to use not only a low molecular liquid crystal compound but also a high molecular liquid crystal compound.

The other liquid crystal compounds may be a polymerizable liquid crystal compound or a non-polymerizable liquid crystal compound. A rod-like liquid crystal compound not having a polymerizable group is described in various literatures (for example, Y. Goto et. al., Mol. Cryst. Liq. Cryst. 1995, Vol. 260, pp. 23-28).

A polymerizable rod-like liquid crystal compound can be obtained by introducing a polymerizable group into a rod-like liquid crystal compound. Examples of the polymerizable group include an unsaturated polymerizable group, an epoxy group, and an aziridinyl group, and among them, the unsaturated polymerizable group is preferable, and an ethylenically unsaturated polymerizable group is particularly preferable. The polymerizable group can be introduced into the molecules of the rod-like liquid crystal compound by various methods. The number of polymerizable groups in the polymerizable rod-like liquid crystal compound is preferably 1 to 6, and is more preferably 1 to 3. Examples of the polymerizable rod-like liquid crystal compound include compounds described in Makromol. Chem., Vol. 190, p. 2255 (1989), Advanced Materials Vol. 5, p. 107 (1993), the specification of U.S. Pat. No. 4,683,327A, the specification of U.S. Pat. No. 5,622,648A, the specification of U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081A), JP2001-328973A, and the like. Two or more types of polymerizable rod-like liquid crystal compounds may be used together. In a case where two or more types of polymerizable rod-like liquid crystal compounds are used together, it is possible to decrease an alignment temperature.

The added amount of the other liquid crystal compounds is not particularly limited, but is preferably 0 to 70 mass %, is more preferably 0 to 50 mass %, and is even more preferably 0 to 30 mass %, with respect to the mass of solid contents of the polymerizable composition. However, the added amount of the other liquid crystal compounds is not limited to the range described above. In the polymerizable composition, a mass ratio of the polymerizable compound represented by Formula (I) to the other liquid crystal compounds (Mass of Polymerizable Compound represented by Formula (I)/Mass of Other Liquid Crystal Compounds) may be 100/0 to 30/70, is preferably 100/0 to 50/50, and is more preferably 100/0 to 70/30. The ratio can be adjusted to be in a preferred range according to the application.

[Chiral Compound]

The polymerizable composition may contain a chiral compound. By using the chiral compound, it is possible to prepare the polymerizable composition as a composition having a cholesteric liquid crystalline phase. The chiral compound may be a liquid crystalline chiral compound, or may be a non-liquid crystalline chiral compound. The chiral compound can be selected from various known chiral agents (for example, described in Liquid Crystal Device Handbook, Chap. 3, Sec. 4-3, Chiral Agent for TN and STN, p. 199, Japan Society for the Promotion of Science, edited by The 142-nd Committee, 1989). In general, the chiral compound has an asymmetric carbon atom, and an axially asymmetric compound or a planarly asymmetric compound which does not has an asymmetric carbon atom can be used. Examples of the axially asymmetric compound or the planarly asymmetric compound include binaphthyl, helicene, paracyclophane, and derivatives thereof. The chiral compound (a chiral agent) may have a polymerizable group. In a case where the chiral compound has a polymerizable group, and the rod-like liquid crystal compound to be used together also has a polymerizable group, it is possible to form a polymer having a repeating unit derived from the rod-like liquid crystal compound and a repeating unit derived from the chiral compound by a polymerization reaction between a polymerizable chiral compound and a polymerizable rod-like liquid crystal compound. Therefore, the polymerizable group in the polymerizable chiral compound is a polymerizable rod-like liquid crystal compound, and in particularly, is preferably a group identical to the polymerizable group in the polymerizable compound represented by Formula (I). Accordingly, the polymerizable group of the chiral compound is preferably an unsaturated polymerizable group, an epoxy group, or an aziridinyl group, is more preferably an unsaturated polymerizable group, and is particularly preferably an ethylenically unsaturated polymerizable group.

In the polymerizable composition, it is preferable that the content of the chiral compound is 1 to 30 mol % with respect to the total number of moles of a liquid crystal compound containing the polymerizable compound represented by Formula (I). It is preferable that a use amount of the chiral compound is small since a small amount of chiral compound does not tend to affect liquid crystallinity. Accordingly, a compound which has a strong twisting force such that twisted alignment at a desired spiral pitch can be attained even in a case where a small amount of chiral compound is used is preferable as the chiral compound. Examples of such a chiral agent having a strong twisting force include a chiral agent described in JP2003-287623A. In addition, chiral agents described in JP2002-302487A, JP2002-80478A, JP2002-80851A, and JP2014-034581A, LC-756 manufactured by BASF SE, and the like are included.

A film formed by setting the polymerizable composition containing the chiral compound to a cholesteric liquid crystalline phase, and then by immobilizing the cholesteric liquid crystalline phase has selective reflection properties with respect to light at a predetermined wavelength according to a spiral pitch, and is useful as a reflection film (for example, a visible light reflection film or an infrared ray reflection film). By using the polymerizable compound represented by Formula (I) which has low birefringence, there is an advantage in that a reflection wavelength range becomes narrower, and selectivity becomes higher, compared to a film having the same thickness in which a liquid crystal compound having higher birefringence is used.

[Polymerization Initiator]

It is preferable that the polymerizable composition contains a polymerization initiator. For example, in an aspect where a cured film is formed by performing a curing reaction by ultraviolet ray irradiation, it is preferable that a polymerization initiator to be used is a photopolymerization initiator which can initiate a polymerization reaction by ultraviolet ray irradiation. Examples of the photopolymerization initiator include an α-carbonyl compound (described in the specification of each of U.S. Pat. No. 2,367,661A and 2,367,670A), acyloin ether (described in the specification of U.S. Pat. No. 2,448,828A), an α-hydrocarbon-substituted aromatic acyloin compound (described in the specification of U.S. Pat. No. 2,722,512A), a polynuclear quinone compound (described in the specification of each of U.S. Pat. No. 3,046,127A and 2,951,758A), a combination between a triaryl imidazole dimer and p-aminophenyl ketone (described in the specification of U.S. Pat. No. 3,549,367A), an acridine compound and a phenazine compound (described in JP1985-105667A (JP-S60-105667A) and in the specification of U.S. Pat. No. 4,239,850A), an oxadiazole compound (described in the specification of U.S. Pat. No. 4,212,970A), and the like.

The content of the photopolymerization initiator in the polymerizable composition is preferably 0.1 to 20 mass %, and is more preferably 1 to 8 mass %, with respect to the mass of solid contents of the polymerizable composition.

[Alignment Control Agent]

An alignment control agent which contributes to stable or prompt formation of a liquid crystalline phase (for example, a cholesteric liquid crystalline phase) may be added to the polymerizable composition. Examples of the alignment control agent include a fluorine-containing (meth)acrylate-based polymer, compounds represented by General Formulas (X1) to (X3) described in WO2011/162291A, and a compound described in paragraphs [0020] to [0031] of JP2013-47204A. The polymerizable composition may contain two or more types of compounds selected from the compounds described above. The compounds can reduce tilt angles of the molecules of the liquid crystal compound or substantially horizontally align the tilt angles in an air interface of a layer. Furthermore, herein, "horizontal alignment" indicates that a major axis of a liquid crystal molecule is parallel to a surface of a film, but does not indicate that the major axis of the liquid crystal molecule is required to be exactly parallel to the surface of the film, and herein, the "horizontal alignment" indicates alignment in which a tilt angle with respect to a horizontal surface is less than 20 degrees. In a case where the liquid crystal compound is horizontally aligned in the vicinity of the air interface, an alignment defect rarely occurs, and thus, transparency in a visible light range increases. In contrast, in a case where the molecules of the liquid crystal compound are aligned at a large tilt angle, for example, the liquid crystal compound is set to a cholesteric liquid crystalline phase, this is not preferable since a spiral axis thereof is shifted from a normal direction of the surface of the film, and thus, reflectivity decreases or a fingerprint pattern is generated, and haze increases or diffraction properties are exhibited.

Examples of the fluorine-containing (meth)acrylate-based polymer which can be used as the alignment control agent are described in [0018] to [0043] of JP2007-272185A, and the like.

One type of compound may be independently used, or two or more types of compounds may be used together, as the alignment control agent.

The content of the alignment control agent in the polymerizable composition is preferably 0.01 to 10 mass %, is more preferably 0.01 to 5 mass %, and is particularly preferably 0.02 to 1 mass %, with respect to the mass of the compound represented by Formula (I).

[Cross-Linking Agent]

The polymerizable composition may arbitrarily contain a cross-linking agent in order to improve a film hardness after being cured and to improve durability. A cross-linking agent which is cured by an ultraviolet ray, heat, humidity, and the like can be preferably used as the cross-linking agent.

The cross-linking agent is not particularly limited, but can be suitably selected according to the purpose, and examples of the cross-linking agent include a polyfunctional acrylate compound such as trimethylol propane tri(meth)acrylate, pentaerythritol tri(meth)acrylate, and pentaerythritol tetraacrylate; an epoxy compound such as glycidyl (meth) acrylate and ethylene glycol diglycidyl ether; an aziridine compound such as 2,2-bishydroxy methyl butanol-tris[3-(1-aziridinyl) propionate] and 4,4-bis(ethylene iminocarbonyl amino) diphenyl methane; an isocyanate compound such as hexamethylene diisocyanate and biuret type isocyanate; a polyoxazoline compound having an oxazoline group in a side chain; an alkoxy silane compound such as vinyl trimethoxy silane and N-(2-aminoethyl)3-aminopropyl trimethoxy silane, and the like. In addition, a known catalyst can be used according to the reactivity of the cross-linking agent, and thus, productivity can be improved in addition to the improvement in the film hardness and the durability. One type of the compound may be independently used, or two or more types thereof may be used together.

The content of the cross-linking agent is preferably 3 mass % to 20 mass %, and is more preferably 5 mass % to 15 mass %, with respect to the mass of solid contents of the polymerizable composition. In a case where the content of the cross-linking agent is greater than or equal to 3 mass %, a cross-linking density improvement effect further increases, and in a case where the content of the cross-linking agent is less than or equal to 20 mass %, stability of a cholesteric liquid crystal layer becomes higher.

[Other Additives]

The polymerizable composition may contain one type or two or more types of other additives such as an antioxidant, an ultraviolet absorbent, a sensitizing agent, a stabilizer, a plasticizer, a chain transfer agent, a polymerization inhibitor, an anti-foaming agent, a leveling agent, a thickener, a flame retardant, a surface-active substance, a dispersant, and a coloring material such as a dye and pigment.

<Film>

The polymerizable compound represented by Formula (I) is useful as a material of various optical films such as a phase difference film and a reflection film, and can form various optical films by using the polymerizable composition containing the polymerizable compound represented by Formula (I).

[Manufacturing Method of Film]

An example of a manufacturing method of the optical film is a method, including at least:

(i) applying the polymerizable composition containing the polymerizable compound represented by Formula (I) onto a surface of a substrate or the like, and setting the polymerizable composition to be in a state of a liquid crystalline phase (a cholesteric liquid crystalline phase or the like); and (ii) performing a curing reaction with respect to the polymerizable composition, and forming a cured film by immobilizing the liquid crystalline phase.

The steps of (i) and (ii) are repeated a plurality of times, and thus, it is possible to prepare a film in which a plurality of cured films described above are laminated. In addition, the plurality of cured films are bonded to each other by an adhesive, and thus, it is also possible to prepare the film in which the plurality of cured films are laminated.

In the step of (i), first, the polymerizable composition is applied onto the surface of the substrate or the surface of an alignment film formed on the substrate. It is preferable that the polymerizable composition is prepared as a coating liquid in which a material is dissolved and/or dispersed in a solvent. An organic solvent is preferably used as the solvent which is used for preparing the coating liquid. Examples of the organic solvent include amide (for example, N,N-dimethyl formamide); sulfoxide (for example, dimethyl sulfoxide); a heterocyclic compound (for example, pyridine); hydrocarbon (for example, benzene and hexane); alkyl halide (for example, chloroform and dichloromethane); ester (for example, methyl acetate and butyl acetate); ketone (for example, acetone and methyl ethyl ketone); ether (for example, tetrahydrofuran and 1,2-dimethoxy ethane); 1,4-butane diol diacetate, and the like. Among them, the alkyl halide and the ketone are particularly preferable. Two or more types of the organic solvents may be used together.

The coating liquid can be applied by various methods such as a wire bar coating method, an extrusion coating method, a direct gravure coating method, a reverse gravure coating method, and a die coating method. In addition, the composition is ejected from a nozzle of an ink jet device, and thus, the coated film can be formed.

Next, the polymerizable composition which is applied onto the surface and becomes the coated film is set to be in the state of the liquid crystalline phase such as a cholesteric liquid crystalline phase. In an aspect where the polymerizable composition is prepared as a coating liquid containing a solvent, there is a case where the coated film is dried, and the solvent is removed, and thus, it is possible to set the polymerizable composition to be in the state of the liquid crystalline phase. In addition, in order to set a transition temperature with respect to the liquid crystalline phase, as desired, the coated film may be heated. For example, first, the coated film is heated to a temperature of an isotropic phase, and then, is cooled to a liquid crystalline phase transition temperature, and the like, and thus, it is possible to stably set the polymerizable composition to be in the state of the liquid crystalline phase. The liquid crystalline phase transition temperature of the polymerizable composition is preferably in a range of 10° C. to 250° C., and is more preferably in a range of 10° C. to 150° C., from the viewpoint of manufacturing suitability or the like. In a case where the liquid crystalline phase transition temperature of the polymerizable composition is lower than 10° C., a cooling step or the like is required in order to decrease the temperature to a temperature range in which the liquid crystalline phase is exhibited. In addition, in a case where the liquid crystalline phase transition temperature of the polymerizable composition is higher than 200° C., first, a high temperature is required in order to set the polymerizable composition to be in an isotropic liquid state at a temperature higher than the temperature range in which the liquid crystalline phase is exhibited, and thus, this is disadvantageous from the viewpoint of the waste of thermal energy, the deformation of the substrate, deterioration, and the like.

Next, in the step of (ii), the coated film which is in the state of the liquid crystalline phase is cured. The curing may be performed by any polymerization method such as a radical polymerization method, an anionic polymerization method, a cationic polymerization method, and a coordination polymerization method. A suitable polymerization method may be selected according to the polymerizable compound represented by Formula (I). By this polymerization, it is possible to obtain a polymer having a unit derived from the polymerizable compound represented by Formula (I) in a constitutional unit.

In an example, a curing reaction is performed by ultraviolet ray irradiation. In the ultraviolet ray irradiation, a light source such as an ultraviolet ray lamp is used. In this step, the curing reaction of the composition is performed by the ultraviolet ray irradiation, and thus, the liquid crystalline phase (the cholesteric liquid crystalline phase or the like) is immobilized, and the cured film is formed.

An irradiation energy amount of an ultraviolet ray is not particularly limited, but in general, is preferably approximately 0.1 J/cm$^2$ to 0.8 J/cm$^2$. In addition, a time for performing the ultraviolet ray irradiation with respect to the coated film is not particularly limited, and may be determined from the viewpoint of both of a sufficient hardness and sufficient productivity of the cured film.

In order to accelerate the curing reaction, the ultraviolet ray irradiation may be performed under heating conditions. In addition, it is preferable that a temperature at the time of performing the ultraviolet ray irradiation is maintained in a temperature range where the liquid crystalline phase is exhibited such that the liquid crystalline phase is not scattered. In addition, an oxygen concentration in the atmosphere is associated with a degree of polymerization, and thus, in a case where a desired degree of polymerization is not attained in the air, and the film hardness is insufficient, it is preferable to decrease the oxygen concentration in the atmosphere by a method such as nitrogen substitution.

In the step described above, the liquid crystalline phase is immobilized, and the cured film is formed. Here, a state where alignment of a compound formed of a liquid crystalline phase is retained is the most typical and preferred aspect as a state where the liquid crystalline phase is "immobilized". The state is not only limited to this, and specifically, indicates a state where a layer does not have fluidity, an alignment form is not changed by an external field or an external force, and an immobilized alignment form can be stably retained in a temperature range of generally 0° C. to 50° C., and in a temperature range of −30° C. to 70° C. in more rigorous conditions. In the present invention, it is preferable that the alignment state of the liquid crystalline phase is immobilized by the curing reaction which is performed by the ultraviolet ray irradiation.

Furthermore, in the film, it is sufficient that the optical properties of the liquid crystalline phase are retained in the layer, and finally, it is not necessary that the composition in the cured film has liquid crystallinity in advance. For example, the composition may have a high molecular weight by the curing reaction, and may lose the liquid crystallinity in advance.

The thickness of the cured film described above is not particularly limited. A preferred film thickness may be determined according to the application or according to optical properties to be desired. In general, the thickness is preferably 0.05 to 50 µm, and is more preferably 1 to 35 µm.

[Substrate]

The film may include a substrate. The material and the optical properties of the substrate are not particularly limited insofar as the substrate has self-supporting properties, and supports the cured film described above. The substrate can be selected from a glass plate, a quartz plate, a polymer film, and the like. According to the application, a substrate having high transparency with respect to ultraviolet light may be used. Examples of a polymer film having high transmittance with respect to visible light include polymer films for various optical films which are used as a member of a display device such as a liquid crystal display device. Examples of the substrate include a polyester film such as polyethylene terephthalate (PET), polybutylene terephthalate, and polyethylene naphthalate (PEN); a polycarbonate (PC) film, a polymethyl methacrylate film; a polyolefin film such as polyethylene and polypropylene; a polyimide film, a triacetyl cellulose (TAC) film, and the like. The polyethylene terephthalate film and the triacetyl cellulose film are preferable.

[Alignment Layer]

The film may include an alignment layer between the substrate and the cured film. The alignment layer has a function of more accurately defining an alignment direction of the liquid crystal compound. The alignment layer can be disposed by means such as a rubbing treatment of an organic compound (preferably, a polymer), oblique vapor deposition of an inorganic compound, and formation of a layer having a microgroove. Further, an alignment layer is also known in which an alignment function is generated by applying an electric field, by applying a magnetic field, or by performing light irradiation. It is preferable that the alignment layer is formed by performing a rubbing treatment with respect to a surface of a polymer film.

A polymer of an organic compound is preferable as a material to be used in the alignment layer, a polymer which can be cross-linked by itself or a polymer which is cross-linked by a cross-linking agent is commonly used. It is natural that a polymer having both functions is also used. Examples of the polymer can include a polymer such as polymethyl methacrylate, an acrylic acid/methacrylic acid copolymer, a styrene/malein imide copolymer, polyvinyl alcohol and modified polyvinyl alcohol, poly(N-methylol acryl amide), a styrene/vinyl toluene copolymer, chlorosulfonated polyethylene, nitrocellulose, polyvinyl chloride, chlorinated polyolefin, polyester, polyimide, a vinyl acetate/vinyl chloride copolymer, an ethylene/vinyl acetate copolymer, carboxy methyl cellulose, gelatine, polyethylene, polypropylene, and polycarbonate, and a compound such as a silane coupling agent. Preferred examples of the polymer include a water-soluble polymer such as poly(N-methylol acryl amide), carboxy methyl cellulose, gelatine, polyvinyl alcohol and modified polyvinyl alcohol, and among them, the gelatine, and the polyvinyl alcohol and the modified polyvinyl alcohol are preferable, and in particular, the polyvinyl alcohol and the modified polyvinyl alcohol are preferable.

[Adhesive Layer]

In a case where a plurality of cured films are bonded to each other by an adhesive, an adhesive layer is disposed between the cured films. The adhesive layer may be formed of an adhesive.

Examples of the adhesive include a hot melt type adhesive, a thermal curing type adhesive, a photocuring type adhesive, a reaction curing type adhesive, and a pressure sensitive adhesive type adhesive which is not necessary to be cured, from the viewpoint of a curing method, and a compound such as an acrylate-based compound, a urethane-based compound, a urethane acrylate-based compound, an epoxy-based compound, an epoxy acrylate-based compound, a polyolefin-based compound, a modified olefin-based compound, a polypropylene-based compound, an ethylene vinyl alcohol-based compound, a vinyl chloride-based compound, a chloroprene rubber-based compound, a cyanoacrylate-based compound, a polyamide-based compound, a polyimide-based compound, a polystyrene-based compound, and a polyvinyl butyral-based compound can be used as the material of each of the adhesives. The photocuring type adhesive is preferable as the curing method from the viewpoint of workability and productivity, and the acrylate-based compound, the urethane acrylate-based compound, the epoxy acrylate-based compound, and the like are preferably used as the material of the adhesive from the viewpoint of optical transparency and heat resistance.

The film thickness of the adhesive layer is 0.5 to 10 µm, and is preferably 1 to 5 µm. In a case where the adhesive layer is used as a half mirror for displaying a projection image, it is preferable that the adhesive layer is disposed with an even film thickness in order to reduce color unevenness or the like.

[Application of Film]

An aspect of the film is a film which is formed by immobilizing alignment (for example, horizontal alignment, vertical alignment, hybrid alignment, and the like) of a liquid crystalline phase of a polymerizable composition, and has optical anisotropy. The film is used as an optical compensation film or the like of a liquid crystal display device or the like.

An aspect of the optical film is a film which includes a layer formed by immobilizing a cholesteric liquid crystalline phase of a polymerizable composition, and has selective reflection properties with respect to light in a predetermined wavelength range. In the cholesteric liquid crystalline phase, liquid crystal molecules are arranged into the shape of a spiral. The layer formed by immobilizing the cholesteric liquid crystalline phase (hereinafter, may be referred to as a "cholesteric liquid crystal layer") functions as a circularly polarized light selective reflection layer which selectively reflects any one of right circularly polarized light and left circularly polarized light in a selective reflection wavelength range, and transmits the other sense of circularly polarized light. A film including one or two or more cholesteric liquid crystal layers can be used in various applications. In a film including two or more cholesteric liquid crystal layers, the senses of circularly polarized light rays which are reflected on the respective cholesteric liquid crystal layers may be identical to each other or opposite to each other according to the application. In addition, the center wavelengths of the selective reflections of the respective cholesteric liquid crystal layers described below may also be identical to each other or different from each other according to the application.

Furthermore, herein, the "sense" of the circularly polarized light indicates whether the circularly polarized light is right circularly polarized light or left circularly polarized light. In the sense of the circularly polarized light, in a case of observing light such that the light propagates towards the front side thereof, a case where a distal end of an electric field vector is rotated in a clockwise direction according to an increase in time is defined as right circularly polarized light, and a case where the distal end of the electric field vector is rotated in a counterclockwise direction is defined as left circularly polarized light. Herein, the term of "sense" may be used in a twisted direction of a spiral of a cholesteric liquid crystal. In the selective reflection of the cholesteric liquid crystal, in a case where the twisted direction (the sense) of the spiral of the cholesteric liquid crystal is in a right direction, the right circularly polarized light is reflected, and the left circularly polarized light is transmitted, and in a case where the sense is in a left direction, the left circularly polarized light is reflected, and the right circularly polarized light is transmitted.

For example, a film including a cholesteric liquid crystal layer having selective reflection properties in a visible light wavelength range (a wavelength of 400 to 750 nm) can be used as a screen or a half mirror for displaying a projection image. In addition, the film can be used as a color filter or a filter which improves a color purity of display light of a display (for example, refer to JP2003-294948A) by controlling a reflection range.

In addition, the optical film can be used in various applications such as a polarization element, a reflection film, an antireflection film, a view angle compensation film, a holography, and an alignment film, which are constituents of an optical element.

Hereinafter, an application as a member for displaying a projection image, which is a particularly preferred application, will be described.

[Member for Displaying Projection Image]

At a wavelength where projection light is selectively reflected by the function of the cholesteric liquid crystal layer described above, any one sense of the circularly polarized light is reflected, and thus, a projection image can be formed. The projection image may be an image which is displayed on the surface of the member for displaying a projection image and is viewed in this way, or may be a virtual image that emerges from the front of the member for displaying a projection image in a case of being observed by an observer.

A center wavelength $\lambda$ of the selective reflection described above depends on a pitch P (=a cycle of a spiral) of a spiral structure in a cholesteric liquid crystalline phase, and corresponds to a relationship of $\lambda = n \times P$ with an average refractive index n of the cholesteric liquid crystal layer. Furthermore, here, the center wavelength $\lambda$ of the selective reflection of the cholesteric liquid crystal layer indicates a wavelength in a centroid position of a reflection peak of a circularly polarized light reflection spectrum measured from a normal direction of the cholesteric liquid crystal layer. As apparent from the expression described above, the pitch of the spiral structure is adjusted, and thus, the center wavelength of the selective reflection can be adjusted. That is, an n value and a P value are adjusted, and for example, the center wavelength λ is adjusted in order to selectively reflect any one of right circularly polarized light and left circularly polarized light with respect to blue light, and thus, it is possible to set the center wavelength of the selective reflection on appearance to be in a wavelength range of 450 nm to 495 nm. Furthermore, the center wavelength of the selective reflection on appearance indicates the wavelength in the centroid position of the reflection peak of the circularly polarized light reflection spectrum of the cholesteric liquid crystal layer measured from an observation direction at the time of being practically used (at the time of being used as the member for displaying a projection image). The pitch of the cholesteric liquid crystalline phase depends on the type of chiral agent which is used along with the polymerizable liquid crystal compound, or the addition concentration thereof, and thus, a desired pitch can be obtained by adjusting the type of chiral agent or the addition concentration thereof. Furthermore, methods described in "Introduction of Liquid Crystal Chemical Experiments" of The Japanese Liquid Crystal Society, published by Sigma Publishing Company in 2007, p. 46, and "Liquid Crystal Handbook" of Editorial Committee of Liquid Crystal Handbook, published by MARUZEN-YUSHODO Company, Limited, p. 196 can be used as a measurement method of the sense of the spiral or the pitch.

A half-width $\Delta\lambda$(nm) of the selective reflection wavelength range where circularly polarized light selective reflection is exhibited depends on birefringence $\Delta n$ of the liquid crystal compound and the pitch P described above, and corresponds to a relationship of $\Delta\lambda = \Delta n \times P$. For this reason, the width of the selective reflection wavelength range can be controlled by adjusting $\Delta n$. That is, in the cholesteric liquid crystal layer formed of the composition containing the polymerizable liquid crystal compound having low birefringence of the present invention, it is possible to increase the wavelength selectivity of the selective reflection.

For example, $\Delta\lambda/\lambda$, which is a ratio of the half-width $\Delta\lambda$ of the selective reflection wavelength range to the center wavelength λ of the selective reflection, can be used as an index indicating the wavelength selectivity of the selective reflection. In the film of the present invention, in particular, in the film which is used as a member for displaying a projection image, $\Delta\lambda/\lambda$ is preferably less than or equal to 0.09, and is more preferably less than or equal to 0.07. More specifically, in the cholesteric liquid crystal layer of the film, it is preferable that $\Delta\lambda/\lambda$ satisfies the range described above, and in each of the two or more cholesteric liquid crystal layers of the film including the two or more cholesteric liquid crystal layers, it is preferable that $\Delta\lambda/\lambda$ satisfies the range described above. Furthermore, $\Delta\lambda$'s and λ's of the respective layers may be identical to each other or different from each other.

Each cured film having a center wavelength of selective reflection on appearance in each of a red light wavelength range, a green light wavelength range, and a blue light wavelength range is prepared by using the polymerizable composition described above, and the cured films are laminated, and thus, a member for displaying a projection image which can display a full color projection image can be prepared. Specifically, in a half mirror, it is preferable that cured films having different center wavelengths of selective reflections (for example, different by greater than or equal to 50 nm) in each of ranges of 750 to 620 nm, 630 to 500 nm, and 530 to 420 nm are laminated.

The center wavelength of the selective reflection of each of the cured films is adjusted according to a light emission wavelength range of a light source to be used in projection and a use aspect of the member for displaying a projection image, and thus, a clear projection image with excellent light utilization efficiency can be displayed. In particular, each of the center wavelengths of the selective reflections of the cured films is adjusted according to the light emission wavelength range of the light source to be used in the projection, and the like, and thus, a clear color projection image with excellent light utilization efficiency can be displayed. In particular, the use aspect of the member for displaying a projection image includes an incidence angle of projection light on the surface of the half mirror for displaying a projection image, a projection image observation direction on the surface of the member for displaying a projection image, and the like.

For example, the member for displaying a projection image described above is configured to have transmittance with respect to light in a visible light range, and thus, can be used as a half mirror which can be used as a combiner of a head-up display. The half mirror for displaying a projection image can visibly display an image projected from a projector or the like, and simultaneously, when the half mirror for displaying a projection image is observed from the same surface side as the surface on which the image is displayed, information and scenery on the opposite surface side can be observed.

When the member for displaying a projection image is used as the half mirror for displaying a projection image, it is preferable that the cured film prepared as described above, in particular, a laminate of three or more cured films is disposed on a surface of a base material. It is preferable that the base material is transparent and has low birefringence in a visible light range. Examples of the base material include inorganic glass or a polymer resin (an acrylic resin (acrylic acid esters such as polymethyl (meth)acrylate, and the like), cyclic polyolefin such as polycarbonate, cyclopentadiene-based polyolefin, or norbornene-based polyolefin, polyolefins such as polypropylene, aromatic vinyl polymers such as polystyrene, polyarylate, cellulose acylate, and the like).

The half mirror for displaying a projection image may include an antireflection layer. It is preferable that the antireflection layer is provided on the outermost surface. The antireflection layer may be disposed on the outermost surface which becomes an viewing side at the time of using the half mirror for displaying a projection image, or may be disposed on the outermost surface on the opposite side, and it is preferable that the antireflection layer is disposed on the outermost surface on the viewing side. In a case where the cured film is disposed on the surface of the base material, the antireflection layer may be disposed on both of the surface of on the base material and the surface on the cured film side which becomes the viewing side. According to such a configuration, a double image, which is particularly generated in a case where the birefringence of the base material is high, is rarely generated.

Examples of the antireflection layer include a layer having a configuration of a two-layer film in which a film of high refractive index and a film of low refractive index are combined, a layer having a configuration of a three-layer film in which a film of intermediate refractive index, a film of high refractive index, and a film of low refractive index are sequentially laminated, and the like, in addition to a film in which fine surface concavities and convexities are formed.

Configuration examples include a configuration including two layers of a layer of high refractive index/a layer of low refractive index in this order from a lower side, a configuration including three layers having different refractive indices, in which a layer of intermediate refractive index (a layer having a refractive index which is higher than that of a underlayer and is lower than that of a layer of high refractive index)/a layer of high refractive index/a layer of low refractive index are laminated in this order, and the like, and it is also proposed that more antireflection layers are laminated. Among them, it is preferable that a layer of intermediate refractive index/a layer of high refractive index/a layer of low refractive index are provided on a hard coat layer in this order, from the viewpoint of durability, optical properties, costs, productivity, and the like, and examples of the configuration include configurations described in JP1996-122504A (JP-H08-122504A), JP1996-110401A (JP-H08-110401A), JP 1998-300902A (JP-H10-300902A), JP2002-243906A, JP2000-111706A, and the like. In addition, an antireflection film having a three-layer configuration, which has excellent robustness with respect to a variation in a film thickness, is described in JP2008-262187A. In a case where the antireflection film having a three-layer configuration described above is disposed on a surface of an image display device, it is possible to set an average value of reflectivity to be less than or equal to 0.5%, to considerably reduce reflected glare, and to obtain an image having excellent stereoscopic effects. In addition, other functions may be imparted to each layer, and examples of a layer to which other functions are imparted include a layer of low refractive index having antifouling properties, a layer of high refractive index having antistatic properties, a hard coat layer having antistatic properties, and a hard coat layer having anti-glare characteristics (for example, JP1998-206603A (JP-H10-206603A), JP2002-243906A, JP2007-264113A, and the like), and the like.

Examples of an inorganic material configuring the antireflection layer include $SiO_2$, SiO, $ZrO_2$, $TiO_2$, TiO, $Ti_2O_3$, $Ti_2O_5$, $Al_2O_3$, $Ta_2O_5$, $CeO_2$, MgO, $Y_2O_3$, $SnO_2$, $MgF_2$, $WO_3$, and the like, and one type of material can be independently used, or two or more types thereof can be used together. Among them, $SiO_2$, $ZrO_2$, $TiO_2$, and $Ta_2O_5$ are preferable since vacuum vapor deposition can be performed at a low temperature, and thus, a film can also be formed on a surface of a plastic substrate.

A laminated structure of alternately forming a high refractive index material layer and a low refractive index material layer, in which the total optical film thickness of a $ZrO_2$ layer and a $SiO_2$ layer from the substrate side is $\lambda/4$, an optical film thickness of the $ZrO_2$ layer is $\lambda/4$, and an optical film thickness of the $SiO_2$ layer which is the outermost layer is $\lambda/4$, is exemplified as a multilayer film which is formed of the inorganic material. Here, $\lambda$ is a design wavelength, and a wavelength of 520 nm is generally used. It is preferable that the outermost layer is formed of $SiO_2$ since a refractive index is low, and a mechanical hardness can be imparted to the antireflection layer.

In a case where the antireflection layer is formed of the inorganic material, for example, a vacuum vapor deposition method, an ion plating method, a sputtering method, a CVD method, a method of performing precipitation in a saturated solution by a chemical reaction, and the like can be adopted as a film formation method.

Examples of an organic material which is used in the layer of low refractive index can include a tetrafluoroethylene-hexafluoropropylene copolymer (FFP), polytetrafluoroethylene (PTFE), an ethylene-tetrafluoroethylene copolymer (ETFE), and the like, and a composition containing a fluorine-containing curable resin and inorganic fine particles, which is described in JP2007-298974A, a low refractive index coating composition containing hollow silica fine particles, which is described in JP2002-317152A, JP2003-202406A, and JP2003-292831A can be preferably used. The film formation method can be performed by coating methods such as a spin coating method, a dip coating method, and a gravure coating method, which have excellent productivity, in addition to the vacuum vapor deposition method.

It is preferable that the refractive index of the layer of low refractive index is preferably 1.30 to 1.51. The refractive index of the layer of low refractive index is more preferably 1.30 to 1.46, and is even more preferably 1.32 to 1.38.

Examples of an organic material which is used in the layer of intermediate refractive index and the layer of high refractive index can include a binder which is obtained by cross-linking or a polymerization reaction, such as an ionizing radiation curable compound having an aromatic ring, an ionizing radiation curable compound containing a halogenated element other than fluorine (for example, Br, I, Cl, and the like), and an ionizing radiation curable compound containing an atom such as S, N, and P, and inorganic particles containing $TiO_2$ to be added to the binder as a main component. Specifically, an organic material described in paragraphs [0074] to [0094] of JP2008-262187A can be exemplified.

The refractive index of the layer of high refractive index is preferably 1.65 to 2.20, and is more preferably 1.70 to 1.80. The refractive index of the layer of intermediate refractive index is adjusted to be a value between the refractive index of the layer of low refractive index and the refractive index of the layer of high refractive index. The refractive index of the layer of intermediate refractive index is preferably 1.55 to 1.65, and is more preferably 1.58 to 1.63.

The film thickness of the antireflection layer is not particularly limited, but may be approximately 0.1 to 10 μm, 1 to 5 μm, and 2 to 4 μm.

EXAMPLES

Hereinafter, the characteristics of the present invention will be described in detail with reference to the examples and comparative examples. Materials, use amounts, ratios, treatment contents, treatment sequences, and the like of the following examples can be suitably changed unless the changes cause deviance from the gist of the present invention. Accordingly, the range of the present invention will not be restrictively interpreted by the following specific examples.

<Synthesis of Compound 1A>

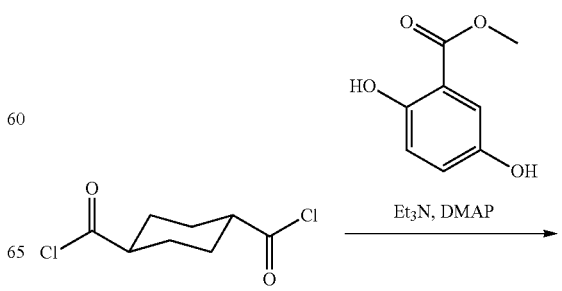

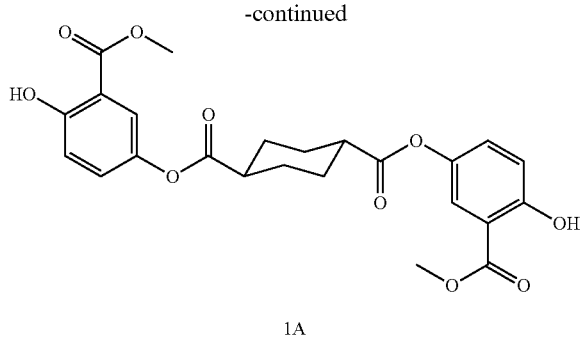

1A

A t-1,4-cyclohexane dicarboxylic acid chloride (9.6 g) and 2-(methoxy carbonyl) hydroquinone (15 g) were stirred in tetrahydrofuran (50 mL). Triethyl amine (15 mL) and N,N-dimethyl aminopyridine (0.56 g) were added at an internal temperature of 2° C., and were stirred at a room temperature for 2 hours. A water layer was removed by adding water and ethyl acetate, and washing was sequentially performed with water and saline. An organic layer was dried with magnesium sulfate, the desiccant was filtered, and then, a solvent was distilled under reduced pressure. Methanol (150 mL) was added, stirring was performed at an internal temperature of 0° C. for 30 minutes, and generated crystals were filtered, and thus, 1.85 g of a compound 1A was obtained.

$^1$H-NMR (Solvent: CDCl$_3$) δ(ppm):
1.6-1.7 (m, 4H), 2.2-2.4 (m, 4H), 2.5-2.6 (m, 2H), 3.9 (s, 6H), 7.0 (d, 2H), 7.2 (dd, 2H), 7.6 (d, 2H)

<Synthesis of Compound 1>

A 4-(4-acryloyloxy butyloxy) benzoic acid was synthesized with reference to a method described in [0085] to [0087] on Page 18 of JP4397550B.

Dibutyl hydroxy toluene (BHT, 60 mg) was added to a tetrahydrofuran (10 mL) solution of methane sulfonyl chloride (1.62 mL), and an internal temperature was cooled to −5° C. A tetrahydrofuran (8 mL) solution of 4-(4-acryloyloxy butyloxy) benzoic acid (5.5 g) and diisopropyl ethyl amine (3.7 mL), which was separately prepared, was subjected to dropwise addition such that an internal temperature did not become higher than or equal to 0° C. Stirring was performed at −5° C. for 1 hour, and then, a small amount of N-methyl imidazole was added, the compound 1A (6.2 g) was added, and 5 mL of tetrahydrofuran was added, and then, triethyl amine (3.1 mL) was subjected to dropwise addition, and after that, stirring was performed at a room temperature for 3 hours. The reaction was stopped by adding water (13 mL), a water layer was removed by adding ethyl acetate, and washing was sequentially performed with a dilute hydrochloric acid and saline. Filtration was performed by adding a desiccant, and then, generated crystals were filtered by adding methanol (15 mL), and thus, 8.5 g of a compound 1 was obtained.

$^1$H-NMR (Solvent: CDCl$_3$) δ(ppm):
1.65-1.8 (m, 4H), 1.85-1.95 (m, 8H), 2.3-2.4 (m, 4H), 2.6-2.7 (m, 2H), 3.9 (s, 6H), 4.1 (m, 4H), 4.15-4.25 (m, 4H), 5.85 (dd, 2H), 6.1 (dd, 2H), 6.4 (dd, 2H), 7.0 (d, 4H), 7.25 (d, 2H), 7.35 (dd, 2H), 7.8 (d, 2H), 8.15 (d, 4H)

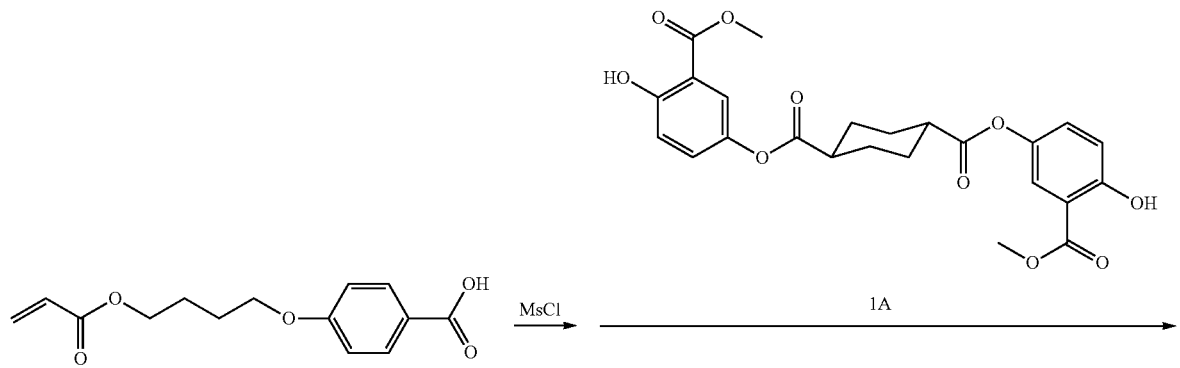

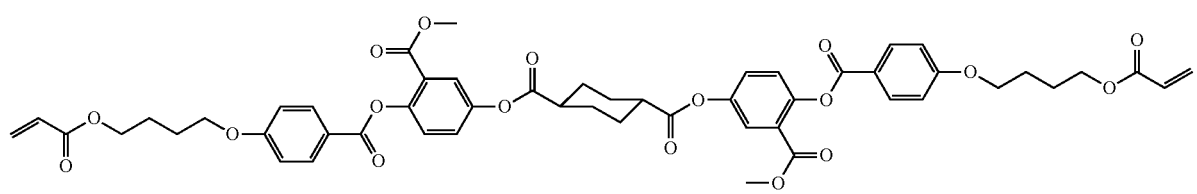

1

<Synthesis of Compound 3>
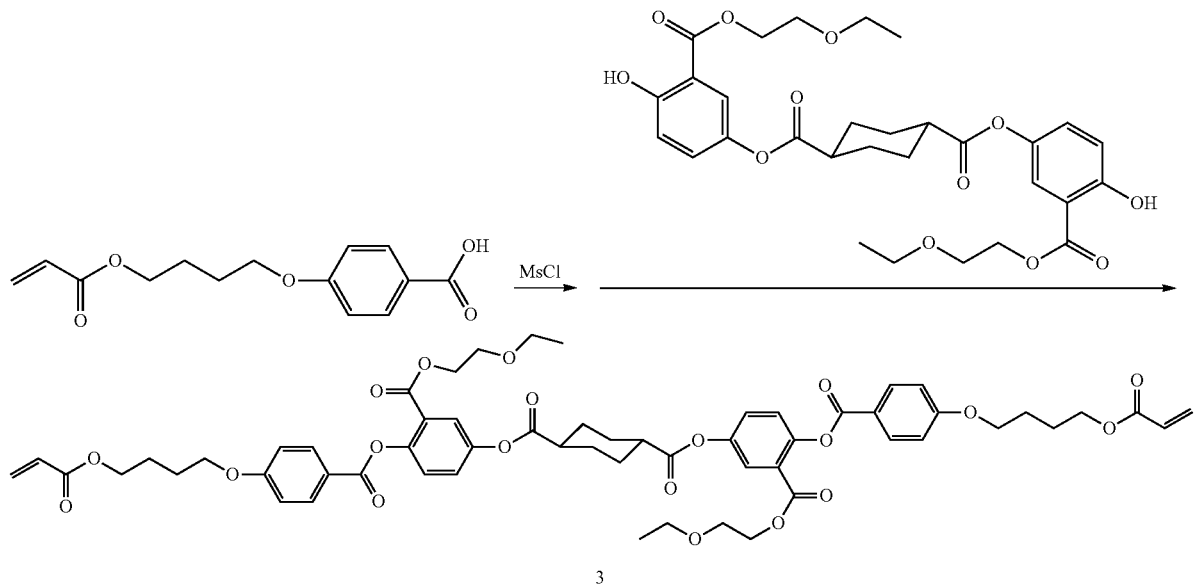
A compound 3 was obtained by using the same synthesis method as that of the compound 1.
¹H-NMR (Solvent: CDCl₃) δ(ppm):
1.2 (t, 6H), 1.65-1.8 (m, 4H), 1.85-1.95 (m, 8H), 2.3-2.4 (m, 4H), 2.6-2.7 (m, 2H), 3.4 (q, 4H), 3.5-3.6 (m, 4H), 4.1 (m, 4H), 4.15-4.25 (m 8H), 5.85 (dd, 2H), 6.1 (dd, 2H), 6.4 (dd, 2H), 7.0 (d, 4H), 7.25 (d, 2H), 7.35 (dd, 2H), 7.8 (d, 2H), 8.15 (d, 4H)
<Synthesis of Compound 4>
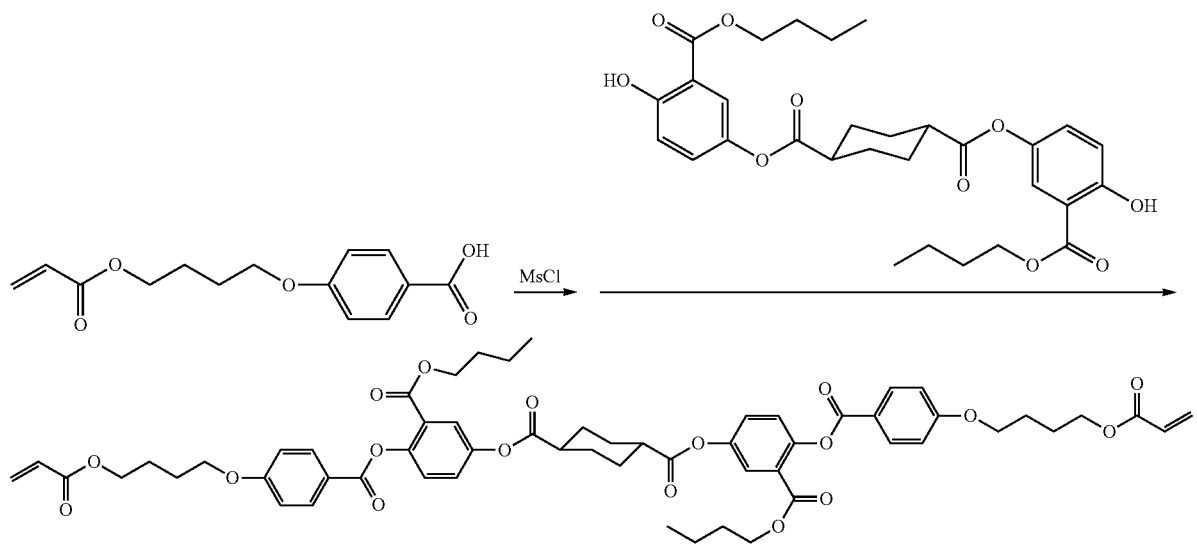
A compound 4 was obtained by using the same synthesis method as that of the compound 1.
¹H-NMR (Solvent: CDCl₃) δ(ppm):
1.0 (t, 6H), 1.65-1.8 (m, 12H), 1.85-1.95 (m, 8H), 2.3-2.4 (m, 4H), 2.6-2.7 (m, 2H), 4.1 (m, 4H), 4.15-4.25 (m, 8H), 5.85 (dd, 2H), 6.1 (dd, 2H), 6.4 (dd, 2H), 7.0 (d, 4H), 7.25 (d, 2H), 7.35 (dd, 2H), 7.8 (d, 2H), 8.15 (d, 4H)

<Synthesis of Compound 2>
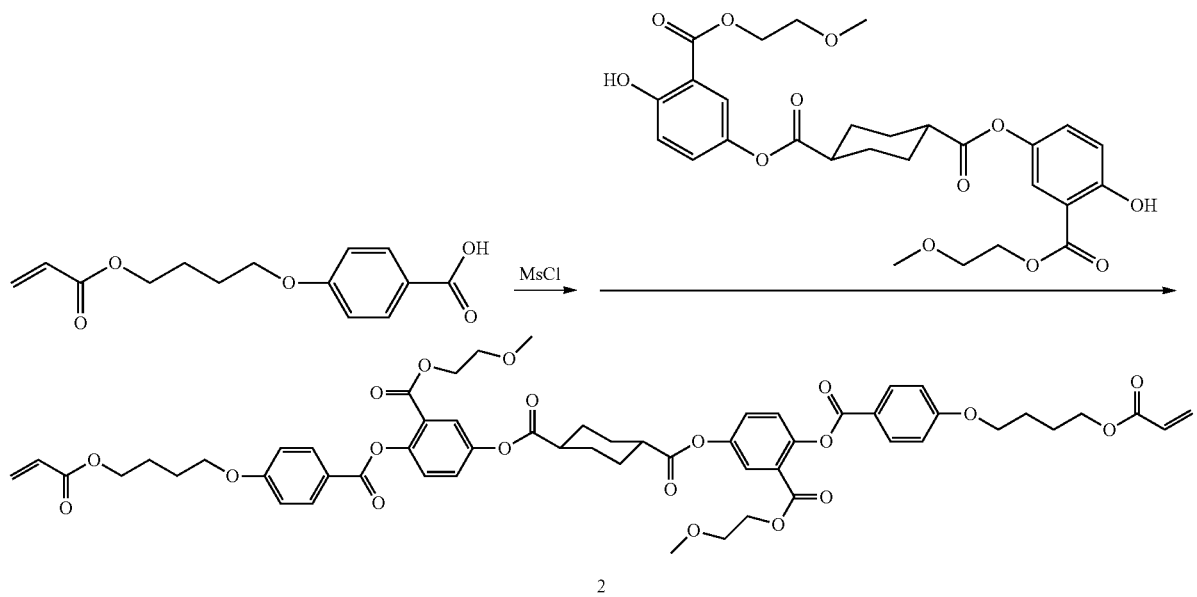
A compound 2 was obtained by using the same synthesis method as that of the compound 1.
¹H-NMR (Solvent: CDCl₃) δ(ppm):
1.65-1.8 (m, 4H), 1.85-1.95 (m, 8H), 2.3-2.4 (m, 4H), 2.6-2.7 (m, 2H), 3.5 (s, 6H), 3.6-3.7 (q, 4H), 4.15-4.4 (m, 12H), 5.85 (dd, 2H), 6.1 (dd, 2H), 6.4 (dd, 2H), 7.0 (d, 4H), 7.25 (d, 2H), 7.35 (dd, 2H), 7.8 (d, 2H), 8.15 (d, 4H)
<Synthesis of Compound 5>
A compound 5 was obtained by using the same synthesis method as that of the compound 1.
¹H-NMR (Solvent: CDCl₃) δ(ppm):
0.9-1.0 (m, 12H), 1.2-1.3 (m, 2H), 1.65-1.9 (m, 16H), 2.3-2.4 (m, 4H), 2.6-2.7 (m, 2H), 4.1-4.25 (m, 12H), 5.85 (dd, 2H), 6.1 (dd, 2H), 6.4 (dd, 2H), 7.0 (d, 4H), 7.25 (d, 2H), 7.35 (dd, 2H), 7.8 (d, 2H), 8.15 (d, 4H)
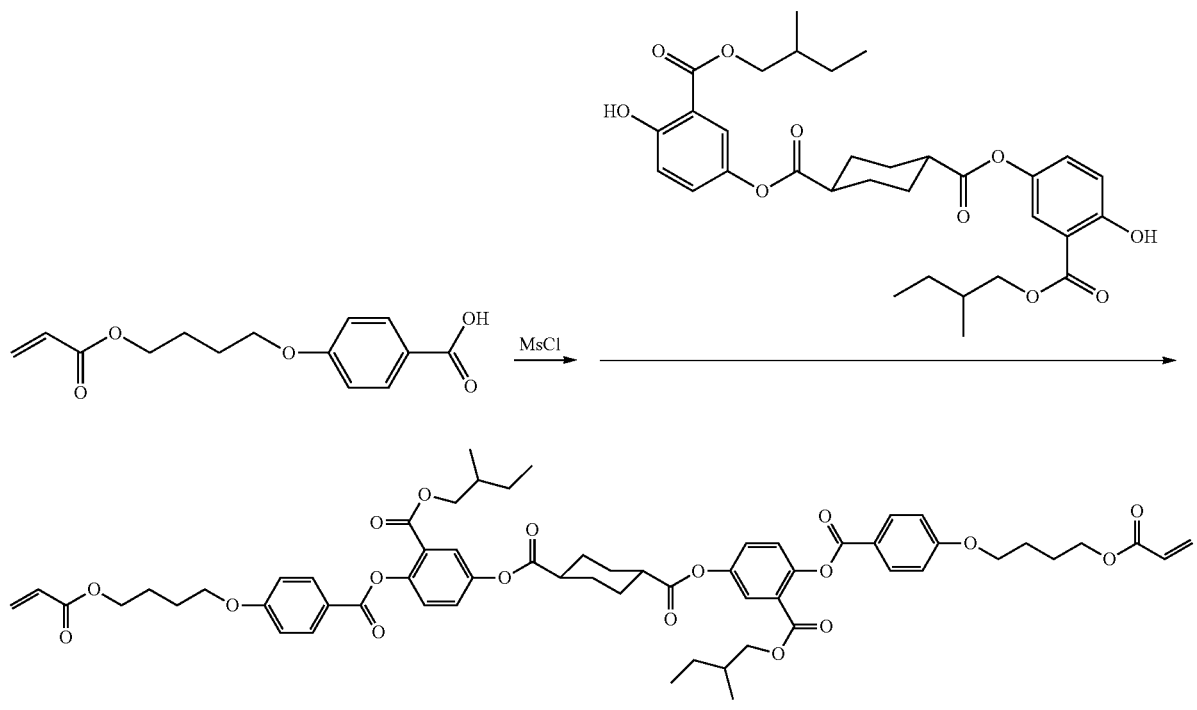

<Synthesis of Compound 23>
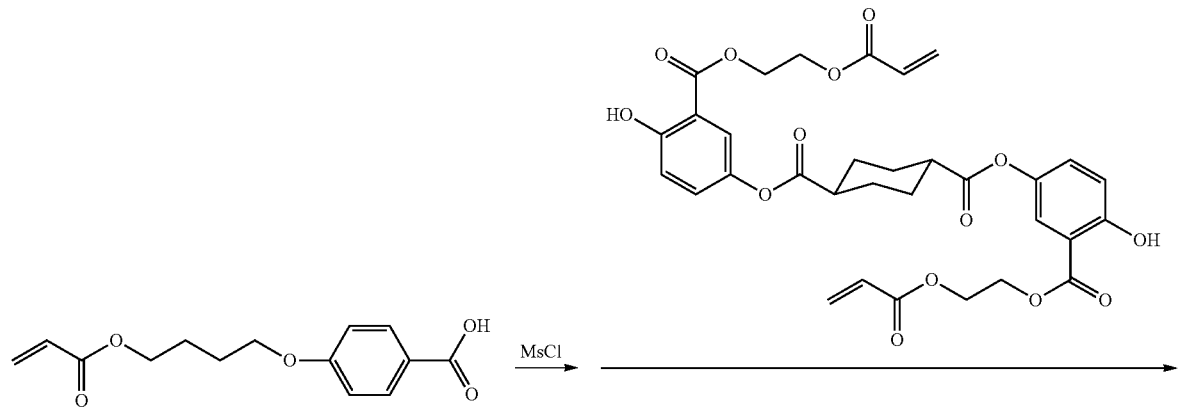
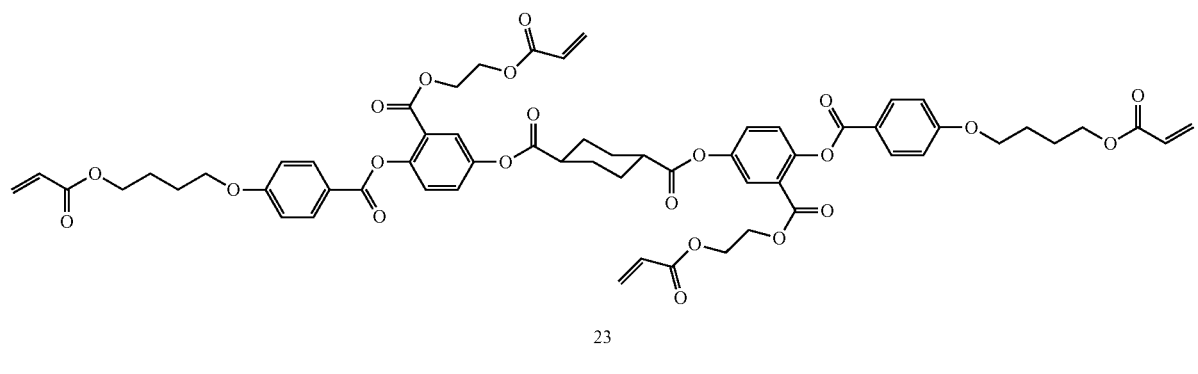
A compound 23 was obtained by using the same synthesis method as that of the compound 1.
$^1$H-NMR (Solvent: CDCl$_3$) δ(ppm):
1.65-1.8 (m, 4H), 1.9-1.95 (m, 8H), 2.3-2.4 (m, 4H), 2.6-2.7 (m, 2H), 4.05-4.15 (m, 4H), 4.2-4.3 (m, 8H), 4.4-4.45 (m, 4H), 5.85 (dd, 4H), 6.0-6.2 (m, 4H), 6.4 (dd, 4H), 6.95 (d, 4H), 7.25 (d, 2H), 7.35 (dd, 2H), 7.8 (d, 2H), 8.15 (d, 4H)
<Synthesis of Compound 24>
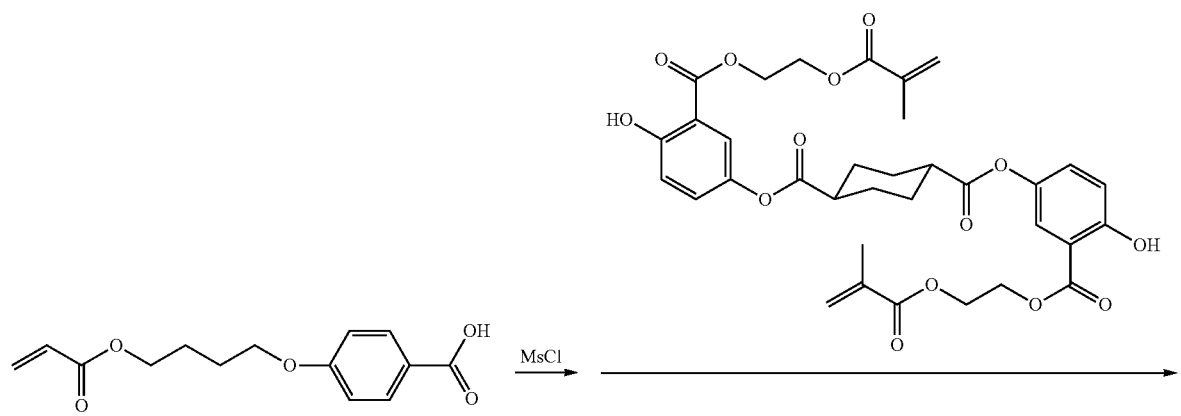

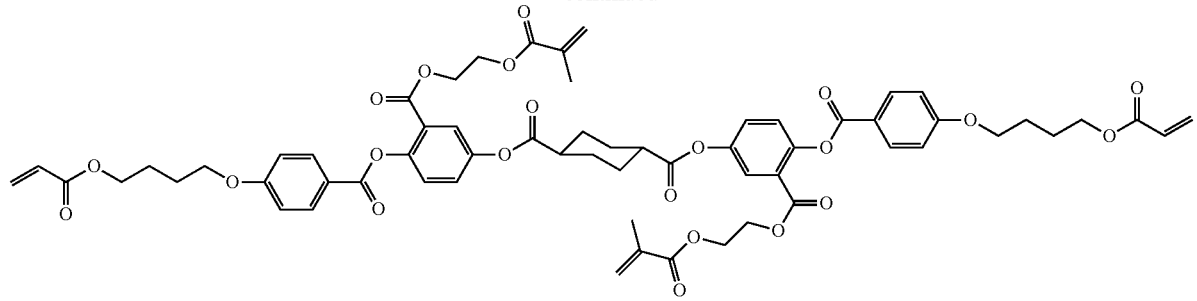
24
A compound 24 was obtained by using the same synthesis method as that of the compound 1.
$^1$H-NMR (Solvent: CDCl$_3$) δ(ppm):
1.65-1.8 (m, 4H), 1.9-2.0 (m, 14H), 2.3-2.4 (m, 4H), 2.6-2.7 (m, 2H), 4.05-4.15 (m, 4H), 4.2-4.35 (m, 8H), 4.4-4.45 (m, 4H), 5.6 (s, 2H), 5.85 (dd, 2H), 6.1-6.2 (m, 4H), 6.4 (dd, 4H), 6.95 (d, 4H), 7.25 (d, 2H), 7.35 (dd, 2H), 7.8 (d, 2H), 8.15 (d, 4H)
<Synthesis of Compound 17>
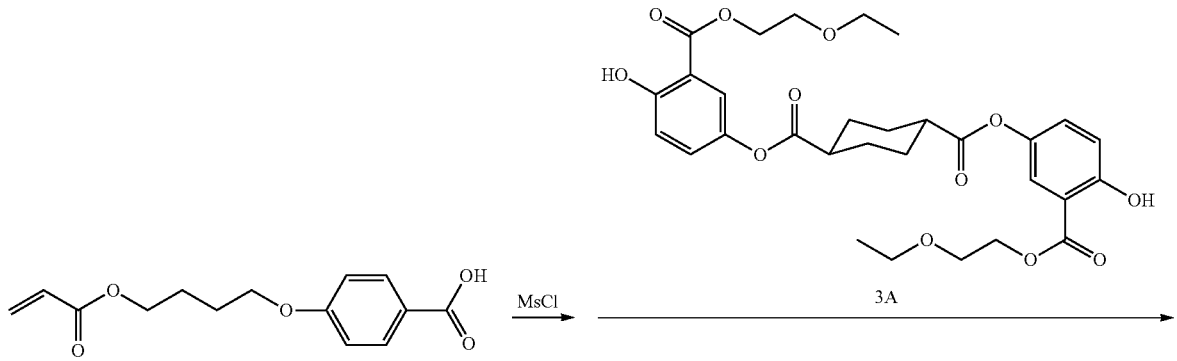
17A
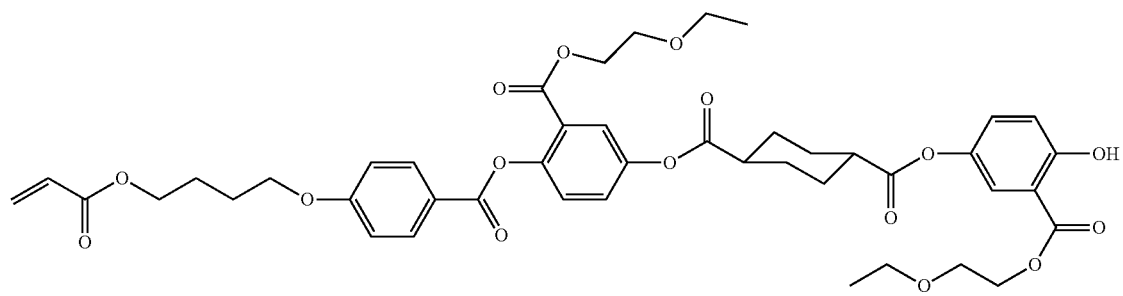
Carboxylic Acid B -continued

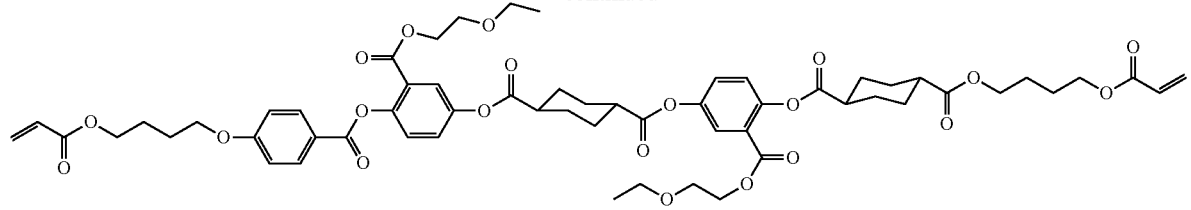

17

Dibutyl hydroxy toluene (BHT, 60 mg) was added to a tetrahydrofuran (10 mL) solution of methane sulfonyl chloride (1.62 mL), and an internal temperature was cooled to −5° C. A tetrahydrofuran (8 mL) solution of a 4-(4-acryloyloxy butyloxy) benzoic acid (5.5 g) and diisopropyl ethyl amine (3.7 mL), which was separately prepared, was subjected to dropwise addition such that an internal temperature did not become higher than or equal to 0° C. Stirring was performed at −5° C. for 1 hour, and then, a small amount of N-methyl imidazole was added, phenol B (15.2 g) was added, and 5 mL of tetrahydrofuran was added, and then, triethyl amine (3.1 mL) was subjected to dropwise addition, and after that, stirring was performed at a room temperature for 3 hours. The reaction was stopped by adding water (13 mL), a water layer was removed by adding ethyl acetate, and washing was sequentially performed with a dilute hydrochloric acid and saline. A crude product obtained by distilling a solvent under reduced pressure was purified by a silica gel column chromatography, and thus, a compound 17A (5.8 g) was obtained.

Next, a carboxylic acid B (1.3 g), paratoluene sulfonyl chloride (TsCl: 1.0 g), and BHT (0.05 g) were stirred in THF (4 mL) and 1-ethyl 2-pyrrolidone (3 mL), 1-methyl imidazole (1.1 mL) was subjected to dropwise addition under ice cooling, and stirring was performed at a room temperature for 1 hour. The compound 17A (3.0 g) was added, and stirring was further performed at a room temperature for 2 hours. Water (2 mL) was added, and then, a water layer was removed, water and methanol were added, stirring was performed for 1 hour under ice cooling, and generated crystals were filtered, and thus, a compound 17 (12.9 g) was obtained.

$^1$H-NMR (Solvent: CDCl$_3$) δ(ppm):
1.15 (t, 3H), 1.25 (t, 3H), 1.4-1.8 (m, 8H), 1.9-2.0 (m, 4H), 2.1-2.2 (m, 2H), 2.25-2.35 (m, 7H), 2.6-2.7 (m, 3H), 3.35 (q, 2H), 3.5-3.6 (m, 4H), 3.7 (q, 2H), 4.05-4.15 (m, 2H), 4.2-4.35 (m, 6H), 4.4-4.45 (m, 2H), 5.85 (dd, 2H), 6.1-6.2 (m, 2H), 6.4 (dd, 2H), 6.95 (d, 2H), 7.1 (d, 1H), 7.2-7.35 (m, 3H), 7.75 (d, 2H), 8.15 (d, 2H)

<Synthesis of Compound 26>

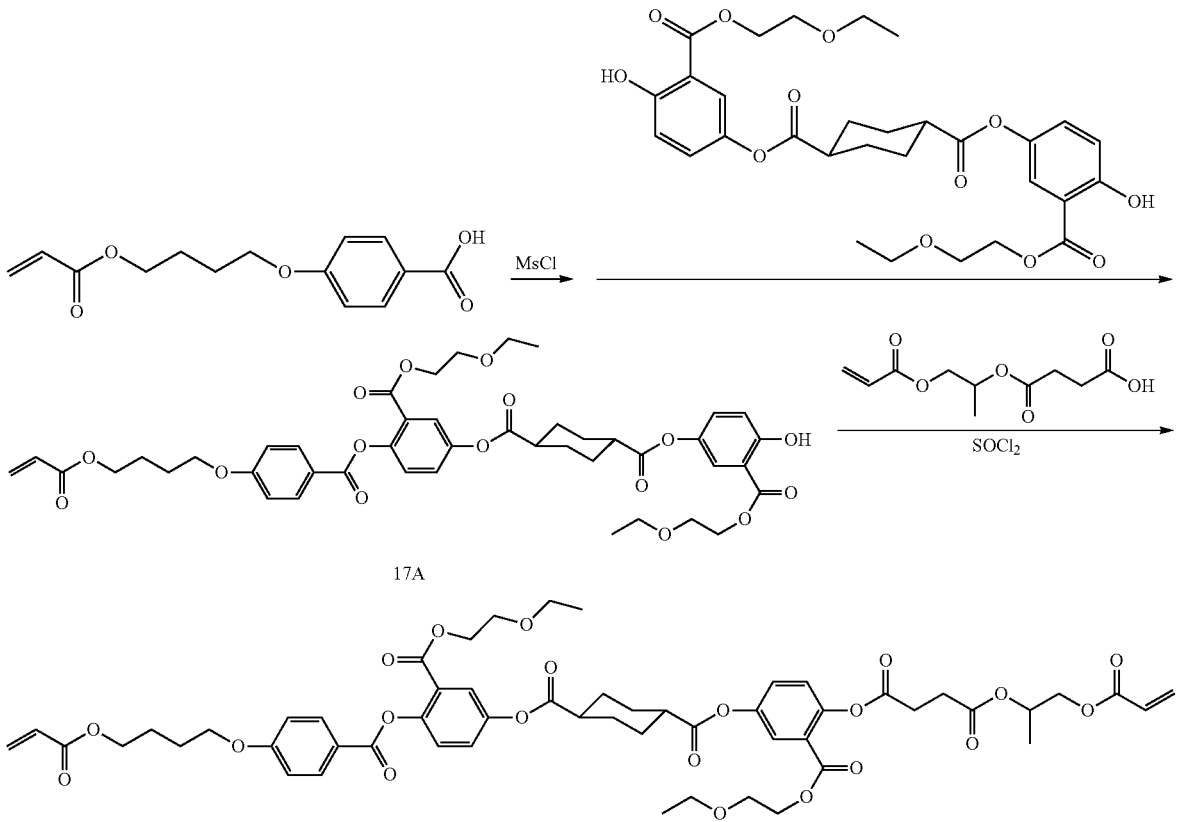

26

A compound 26 was obtained by using the same synthesis method as that of the compound 17.

$^1$H-NMR (Solvent: CDCl$_3$) δ(ppm):

1.15 (t, 3H), 1.2-1.25 (m, 6H), 1.6-1.75 (m, 6H), 1.9-2.0 (m, 4H), 2.3-2.35 (m, 4H), 2.6-2.7 (m, 2H), 2.75-2.85 (m, 2H), 2.95-3.05 (m, 2H), 3.4 (q, 2H), 3.5-3.6 (m, 4H), 3.75 (q, 2H), 4.1-4.35 (m, 8H), 4.4-4.45 (m, 2H), 5.2-5.3 (m, 1H), 5.85 (dd, 2H), 6.1-6.2 (m, 2H), 6.4 (dd, 2H), 6.95 (d, 2H), 7.1 (d, 1H), 7.2-7.35 (m, 3H), 7.75 (d, 2H), 8.15 (d, 2H)

<Measurement of Birefringence>

Birefringences (Δn) of each of the compounds synthesized as described above and a known compound of the related art were measured according to a method described in p. 202 of Liquid Crystal Handbook (Editorial Committee of Liquid Crystal Handbook). Specifically, a sample was injected into a wedge type cell, and was irradiated with laser light at a wavelength of 550 nm, and a refraction angle of transmission light was measured, and thus, Δn at 60° C. was obtained. Liquid crystal compositions in which each of the compounds synthesized as described above or the known compound of the related art (a compound M-1 and a compound M-2) were mixed according to the following table were used as the sample. In the compound 3 and the compound M-1, the precipitation of the crystals was not observed during the measurement, but in the compound M-2, the crystals were precipitated during the measurement, and thus, it was not possible to measure Δn.

<Preparation of Phase Difference Film>

A liquid crystalline composition coating liquid (1) having the following compositions was prepared by using an exemplary compound synthesized in the examples described above.

Compound 1 100 parts by mass
Air Interface Alignment Agent (1) 0.1 parts by mass
Polymerization Initiator IRGACURE 819 (manufactured by BASF SE) 3 parts by mass
Solvent Chloroform 900 parts by mass
Air Interface Alignment Agent (1)

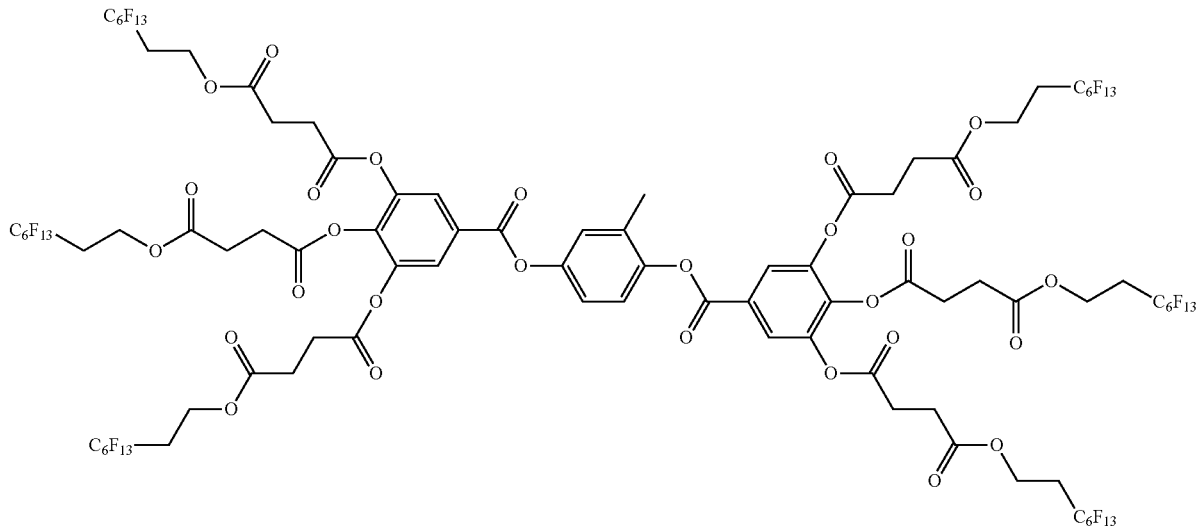

TABLE 1

| Compound | Isotropic Phase Transition Point | Δn at 50° C. |
|---|---|---|
| 3 | 167 | 0.133 |
| M-1 | 123 | 0.175 |
| M-2 | 86 | Unmeasurable |

Next, a washed glass substrate was coated with a polyimide alignment film SE-130 manufactured by Nissan Chemical Industries, Ltd. by a spin coating method, and was dried, and then, was calcinated at 250° C. for 1 hour. A substrate with an alignment film was prepared by performing a rubbing treatment with respect to the polyimide alignment film on the glass substrate. The liquid crystalline composition coating liquid (1) was applied onto a rubbing treatment surface of the alignment film at room temperature by a spin coating method, and was aligned and matured at 120° C. for 30 seconds, and then, light irradiation was performed at 50° C. for 10 seconds under a nitrogen gas atmosphere by using a high pressure mercury lamp, the alignment was immobilized, and thus, a phase difference film 1 was formed. The precipitation of the crystals was not observed on a coated film during a period from the coating to the heating.

The phase difference film 1 obtained by immobilizing the alignment of the liquid crystal composition was observed by a polarization microscope, and then, it was confirmed that the liquid crystal composition was evenly and uniaxially aligned without having an alignment defect. As a result of measuring the film in a Tip-Tilt mode by using AxoScan manufactured by Axometrics, Inc, it was confirmed that the average tilt angle of the liquid crystal calculated by the device was 2.1 degrees, and thus, it was possible to form an A-plate type phase difference film. In addition, Δn at a wavelength of 550 nm calculated from a phase difference which was measured by using the device and a film thickness of the phase difference film which was measured by using a non-contact three-dimensional surface shape measurement system (BW-A501, manufactured by Nikon Corporation) was 0.103.

Phase difference films 2 to 5 were prepared by the same preparation as that of the phase difference film 1 and by using a polymerizable composition coating liquid in which the compound 1 in the polymerizable composition coating liquid (1) was changed to each of the compound 23, the compound 24, the compound 17, and the compound M-2, and Δn was calculated by the same measurement as that of the phase difference film 1. The results are shown in Table 2.

TABLE 2

| Phase Difference Film | Compound | Polymerization Initiator (Parts by Mass) | Air Interface Alignment Agent (1) (Parts by Mass) | Maturing Temperature | Polymerization Temperature | Phase Difference (nm) | Film Thickness (μm) | Δn |
|---|---|---|---|---|---|---|---|---|
| 1 | 3 | 3 | 0.1 | 120 | 70 | 165 | 1.6 | 0.103 |
| 2 | 23 | 3 | 0.1 | 120 | 70 | 162 | 1.61 | 0.101 |
| 3 | 24 | 3 | 0.1 | 120 | 70 | 153 | 1.55 | 0.099 |
| 4 | 17 | 3 | 0.1 | 100 | 50 | 135 | 1.52 | 0.089 |
| 5 | M-1 | 3 | 0.1 | 100 | 50 | 214 | 1.5 | 0.143 |

What is claimed is:

1. A polymerizable compound represented by Formula (I);

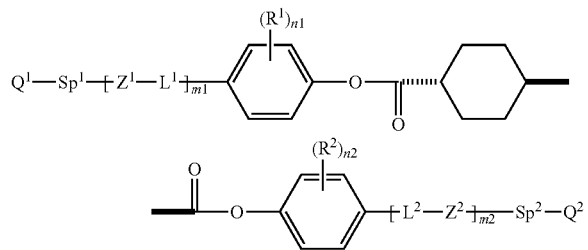

(I)

in the formula, $R^1$ and $R^2$ are each independently a group selected from the group consisting of an alkyl group, an alkoxy group, and —C(=O)—X-$Sp^3$-$Q^3$, n1 and n2 each independently represent an integer of 0 to 4, X represents a single bond, —O—, —S—, or —N($Sp^4$-$Q^4$)-, or represents a nitrogen atom which forms a cyclic structure along with $Q^3$ and $Sp^3$, $Z^1$ represents an arylene group which may have a substituent or a heteroarylene group which may have a substituent, $Z^2$ represents a trans-1,4-cyclohexylene group which may have a substituent, an arylene group which may have a substituent, or a heteroarylene group which may have a substituent, all of the substituents are each independently 1 to 4 substituents selected from the group consisting of an alkyl group, an alkoxy group, and —C(=O)—X-$Sp^3$-$Q^3$, m1 represents an integer of 1 or 2, and m2 represents an integer of 0 to 2, when m1 and m2 represent 2, two $Z^1$'s and $Z^2$'s may be identical to each other or different from each other, $L^1$ and $L^2$ each independently represent a single bond or a linking group selected from the group consisting of —O—, —CH$_2$O—, —OCH$_2$—, —(CH$_2$)$_2$OC(=O)—, —C(=O)O(CH$_2$)$_2$—, —NH—, N(CH$_3$)—, —S—, —C(=O)O—, —OC(=O)—, —OC(=O)O—, —C(=O)N($T^3$)-, —N($T^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, $T^3$ represents -$Sp^5$-$Q^5$, $Sp^1$, $Sp^2$, $Sp^3$, $Sp^4$, and $Sp^5$ each independently represent a single bond or a linking group selected from the group consisting of a linear alkylene group or a branched alkylene group having 1 to 20 carbon atoms, and a group in which one or two or more —CH$_2$—'s in the linear alkylene group or the branched alkylene group having 1 to 20 carbon atoms are substituted with —O—, —S—, —NH—, —N(CH$_3$)—, —C(=O)—, —OC(=O)—, or —C(=O)O—, $Q^1$ and $Q^2$ each independently represent any one polymerizable group selected from the group consisting of groups represented by Formula (Q-1) to Formula (Q-5) below, and $Q^3$, $Q^4$, and $Q^5$ each independently represent any one polymerizable group selected from the group consisting of a hydrogen atom, a cycloalkyl group, a group in which one or two or more —CH$_2$—'s in the cycloalkyl group are substituted with —O—, —S—, —NH—, —N(CH$_3$)—, —C(=O)—, —OC(=O)—, or —C(=O)O—, or groups represented by Formula (Q-1) to Formula (Q-5) below, and may represent a single bond in a case in which $Q^3$ forms a cyclic structure along with X and $Sp^3$, and when $Sp^4$ is a single bond, $Q^4$ is not a hydrogen atom

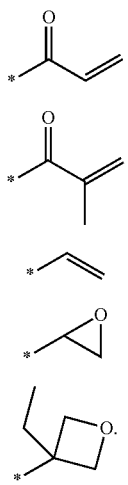

2. The polymerizable compound according to claim 1, wherein $R^1$ and $R^2$ are each —C(=O)—X-$Sp^3$-$Q^3$.

3. The polymerizable compound according to claim 2, wherein X is —O—.

4. The polymerizable compound according to claim 2, wherein $Sp^a$ is any one group selected from the group consisting of a linear alkylene group or a branched alkylene group having 1 to 5 carbon atoms, —(CH$_2$)$_2$—O—(CH$_2$)$_2$—, —CH$_2$—O—(CH$_2$)$_2$—, and —(CH$_2$)$_2$—O—CH$_2$—.

5. The polymerizable compound according to claim 1, wherein m1 is 1, and $Z^1$ is an arylene group which may have a substituent.

6. The polymerizable compound according to claim 1, wherein $Q^1$ and $Q^2$ are each independently a group represented by Formula (Q-1) or a group represented by Formula (Q-2).

7. The polymerizable compound according to claim 1, wherein m2 is 0 or 1, and $Z^2$ is an arylene group which may have a substituent.

8. The polymerizable compound according to claim 5, wherein m2 is 0 or 1, and $Z^2$ is an arylene group which may have a substituent.

9. The polymerizable compound according to claim 1, wherein both of $L^1$ and $L^2$ are —C(=O)O— or —OC(=O)—.

10. The polymerizable compound according to claim 5, wherein both of $L^1$ and $L^2$ are —C(=O)O— or —OC(=O)—.

11. The polymerizable compound according to claim 7, wherein both of $L^1$ and $L^2$ are —C(=O)O— or —OC(=O)—.

12. The polymerizable compound according to claim 1, wherein $R^1$ and $R^2$ are each —C(=O)—O-$Sp^3$-$Q^3$,
$Sp^3$ is any one group selected from the group consisting of a linear alkylene group or a branched alkylene group having 1 to 5 carbon atoms, —(CH$_2$)$_2$—O—(CH$_2$)$_2$—, —CH$_2$—O—(CH$_2$)$_2$—, and —(CH$_2$)$_2$—O—CH$_2$—,
m1 is 1, and $Z^1$ is a phenylene group which may have a substituent,
$Q^1$ and $Q^2$ are each independently a group represented by Formula (Q-1) or a group represented by Formula (Q-2), and
both of $L^1$ and $L^2$ are —C(=O)O— or —OC(=O)—.

13. The polymerizable compound according to claim 12, wherein m2 is 0 or 1, and $Z^2$ is a phenylene group which may have a substituent.

14. A polymer obtained by a polymerization reaction of the polymerizable compound according to claim 1.

15. A polymerizable composition, comprising:
the polymerizable compound according to claim 1.

16. The polymerizable composition according to claim 15, further comprising:
a liquid crystal compound other than the polymerizable compound represented by Formula (I).

17. The polymerizable composition according to claim 15, further comprising:
a cross-linking agent.

18. The polymerizable composition according to claim 15, further comprising:
a polymerization initiator.

19. The polymerizable composition according to claim 15, further comprising:
a chiral compound.

20. A film, comprising:
a cured film of the polymerizable composition according to claim 15.

* * * * *